United States Patent [19]
Lesieur et al.

[11] Patent Number: 6,071,946
[45] Date of Patent: Jun. 6, 2000

[54] TRICYCLIC UREA COMPOUNDS

[75] Inventors: Daniel Lesieur, Gondecourt; Patrick Depreux, Armentieres; Véronique Leclerc, Lille; Hamid Ait Mansour, Roubaix; Philippe Delagrange, Issy-les-Moulineaux; Pierre Renard, Versailles, all of France

[73] Assignee: Adir et Compagnie, Courbevoie, France

[21] Appl. No.: 09/387,461

[22] Filed: Sep. 1, 1999

Related U.S. Application Data

[63] Continuation-in-part of application No. 09/124,197, Jul. 28, 1998, which is a continuation-in-part of application No. 08/545,395, Oct. 19, 1995, Pat. No. 5,843,986.

[30] Foreign Application Priority Data

Oct. 21, 1994 [FR] France ................................ 94.12581

[51] Int. Cl.$^7$ ................... A61K 31/38; A61K 31/335; C07D 407/02; C07D 409/02; C07D 491/042

[52] U.S. Cl. ................... 514/411; 514/443; 514/444; 514/455; 514/468; 548/431; 548/432; 549/44; 549/299; 549/387

[58] Field of Search ................... 514/411, 443, 514/444, 455, 468; 548/431, 432; 549/44, 299, 387

[56] References Cited

U.S. PATENT DOCUMENTS 5,843,986  12/1998  Leiseur et al. .

FOREIGN PATENT DOCUMENTS

| 286515 | 10/1988 | European Pat. Off. . |
|---|---|---|
| 286516 | 10/1988 | European Pat. Off. . |
| 447285 | 9/1991 | European Pat. Off. . |
| 530087 | 3/1993 | European Pat. Off. . |
| 562956 | 9/1993 | European Pat. Off. . |
| 95/29173 | 11/1995 | WIPO . |

OTHER PUBLICATIONS

Glennon et al. in Drug Development Research 22 25–36 (1991).

S. Conway et al. in Society for Neuroscience, 23. Item 420.11 (1997).

*Primary Examiner*—Johann Richter
*Assistant Examiner*—Taofiq A. Solola
*Attorney, Agent, or Firm*—The Firm of Gordon W. Hueschen

[57] ABSTRACT

A compound selected from those of formula (I):

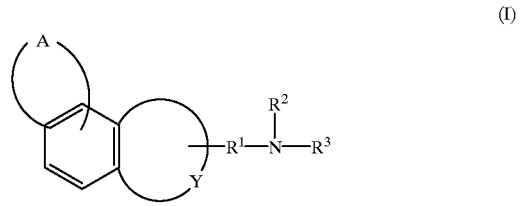

in which A, Y, $R^1$, $R^2$ and $R^3$ are as defined in the Specification, and pharmaceutical compositions containing the same, which are useful for treating a mammal afflicted with a disorder of the melatoninergic system.

14 Claims, No Drawings

TRICYCLIC UREA COMPOUNDS

The present application is a continuation-in-part of our prior-filed copending application Ser. No. 09/124,197 of Jul. 28, 1998, which in turn was a continuation-in-part of our prior-filed application Ser. No. 08/545,395 of Oct. 19, 1995, now U.S. Pat. No. 5,843,986.

The invention relates to new tricyclic carbamide or urea compounds, to their preparation, and to pharmaceutical compositions which contain them and to the use thereof.

Many studies in the last ten years have demonstrated the fundamental role of melatonin (5-methoxy-N-acetyltryptamine) in controlling the circadian rhythm and endocrine functions, and the melatonin receptors have been characterized and localized.

In addition to their beneficial effect on disorders of the circadian rhythm (J. Neurosurg., 1985, 63, pp 321–341) and sleep disorders (Psychopharmacology, 1990, 100, pp 222–226), ligands for the melatoninergic system have advantageous pharmacological properties as regards the central nervous system, in particular anxiolytic and antipsychotic lo properties (Neuropharmacology of Pineal Secretions, 1990, 8 (3–4), pp 264–272) and analgesic properties (Pharmacopsychiat., 1987, 20, pp 222–223), and for the treatment of Parkinson's disease (J. Neurosurg., 1985, 63, pp 321–341) and Alzheimer's disease (Brain Research, 1990, 528, pp 170–174). These compounds have likewise shown activity against certain cancers (Melatonin—Clinical Perspectives, Oxford University Press, 1988, page 164–165), on ovulation (Science 1987, 227, pp 714–720) and against diabetes (Clinical Endocrinology, 1986, 24, pp 359–364).

Compounds which make it possible to act on the melatoninergic system are therefore excellent medicaments which can be used by the clinician in the treatment of the abovementioned pathologies.

The Applicant Company has discovered new tricyclic amide compounds, of novel structure, which show a very high affinity for melatoninergic receptors and which exhibit, in vitro and in vivo, considerable pharmacological and therapeutic advantage.

The invention relates more particularly to the compounds of formula (I):

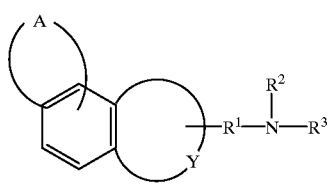
(I)

in which:

$R^1$ represents a ($C_1$–$C_4$)alkylene chain which is unsubstituted or substituted by a radical chosen from alkyl, hydroxyl, alkoxycarbonyl and carboxyl;

$R^2$ represents a hydrogen atom or an alkyl;

$R^3$ represents:

either a group of formula $R^{31}$

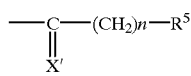
($R^{31}$)

in which n represents zero or an integer from 1 to 3 and $R^5$ represents a hydrogen atom, an unsubstituted or substituted alkyl, an unsubstituted or substituted alkenyl, an unsubstituted or substituted alkynyl, an unsubstituted or substituted cycloalkyl or an unsubstituted or substituted dicycloalkylalkyl; and X' represents an oxygen or sulfur atom;

or a group of formula $R^{32}$:

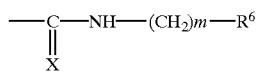
($R^{32}$)

in which X represents an oxygen or sulfur atom, m represents zero or an integer from 1 to 3 and $R^6$ represents a radical chosen from the same values as $R^5$;

A represents a chain of formula —O—$A^1$— in which $A^1$ is a chain chosen from ($C_2$–$C_5$)alkylene, ($C_2$–$C_5$) alkenylene and ($C_2$–$C_5$)alkynylene; $A^1$ being unsubstituted or substituted by one or a number of groups chosen from alkyl, alkoxy, hydroxyl and oxo, Y forming, with the benzene ring to which it is bonded, a $Y^1$ group chosen from naphthalene, partially hydrogenated naphthalene, benzofuran, partially hydrogenated benzofuran, benzothiophene, partially hydrogenated benzothiophene and indole;

it being understood that:

the expression "substituted" relating to the terms "alkyl", "alkenyl" and "alkynyl" means that these groups are substituted by one or a number of radicals chosen from halogen, alkyl and alkoxy, the expression "substituted" relating to the term "cycloalkyl" or "dicycloalkylalkyl" means that these groups are substituted by one or a number of radicals chosen from: alkyl, alkoxy, hydroxyl and the oxo group, the terms "alkyl" and "alkoxy" denote radicals containing from 1 to 6 carbon atoms, the terms "alkenyl" and "alkynyl" denote unsaturated radicals containing 2 to 6 carbon atoms, the term "cycloalkyl" denotes a saturated or unsaturated group containing 3 to 8 carbon atoms, to their enantiomers and diastereoisomers, and to their addition salts with a pharmaceutically acceptable base.

The invention particularly relates to:

the compounds of formula (I) in which $R^1$ represents an ethylene chain, the compounds of formula (I) in which $R^2$ represents a hydrogen atom, the compounds of formula (I) in which $R^3$ represents a group of formula $R^{31}$, the compounds of formula (I) in which $R^5$ represents an alkyl, the compounds of formula (I) in which $R^5$ represents a cycloalkyl group, the compounds of formula (I) in which $R^3$ represents an $R^{32}$ group, the compounds of formula (I) in which $R^6$ represents an alkyl, the compounds of formula (I) in which $R^6$ represents a cycloalkyl,
the compounds of formula (I) in which X' is an oxygen atom,
the compounds of formula (I) in which X' is a sulfur atom,
the compounds of formula (I) in which X is an oxygen atom,
the compounds of formula (I) in which X is a sulfur atom,
the compounds of formula (I) in which $A^1$ is an ethylene chain,
the compounds of formula (I) in which $A^1$ is a trimethylene chain,
the compounds of formula (I) in which $A^1$ is a tetramethylene chain,
the compounds of formula (I) in which $A^1$ is a vinylene chain,
the compounds of formula (I) in which $A^1$ is a propenylene chain,
the compounds of formula (I) in which Y forms, with the benzene ring to which it is bonded, a naphthalene group,
the compounds of formula (I) in which Y forms, with the benzene ring to which it is bonded, a tetrahydronaphthalene group,
the compounds of formula (I) in which Y forms, with the benzene ring to which it is bonded, an indole group.

The invention more particularly relates to:
the compounds of formula $(I_1)$

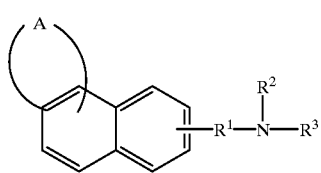

in which A, $R^1$, $R^2$ and $R^3$ are as defined in the formula (I) and the compounds of formula $(I_2)$

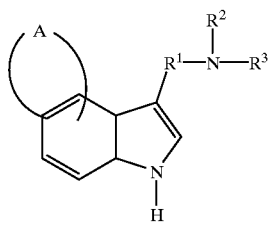

in which A, $R^1$, $R^2$ and $R^3$ are as defined in the formula (I). For example, the invention relates to the compounds of formula $(I_3)$:

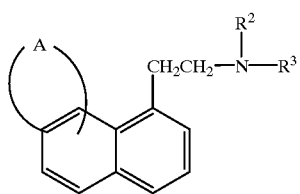

in which A, $R^2$ and $R^3$ are as defined in the formula (I) and to the compounds of formula $(I_4)$

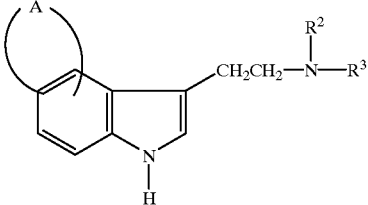

in which A, $R^2$ and $R^3$ are as defined in the formula (I).

Mention may be made, as examples and in a nonlimiting way, among the pharmaceutically acceptable bases which can be used to form an addition salt with the compounds of the invention, of sodium, potassium, calcium or aluminium hydroxides, alkali metal or alkaline-earth metal carbonates and organic bases, such as triethylamine, benzylamine, diethanolamine, tert-butylamine, dicyclohexylamine and arginine.

The alkyl radicals present in the formula (I) can be chosen particularly from methyl, ethyl, n-propyl, isopropyl, n-butyl, isobutyl, sec-butyl, tert-butyl, pentyl or hexyl.

The alkoxy radicals present in the formula (I) can be chosen from methoxy, ethoxy, n-propoxy, isopropoxy, n-butoxy, isobutoxy, sec-butoxy, tert-butoxy, pentyloxy and hexyloxy.

The halogens present in the formula (I) can be chosen from bromine, chlorine, fluorine and iodine.

The cycloalkyls present in the formula (I) can be chosen from cyclopropyl, cyclobutyl, cyclopentyl, cyclohexyl, cycloheptyl and cyclooctyl.

The alkylene groups present in the formula (I) can be chosen from ethylene, trimethylene, tetramethylene and pentamethylene.

The invention also relates to the process for the preparation of the compounds of formula (I), wherein a compound of formula (II):

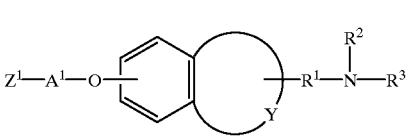

in which $R^1$, $R^2$, $R^3$, $A^1$ and Y have the same definition as in the formula (I) and $Z^1$ represents a reactive functional group,
is cyclized in order to obtain the corresponding compound of formula (I),

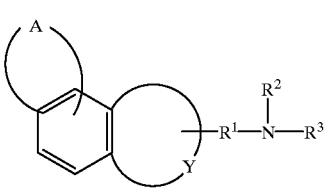

in which $R^1$, $R^2$, $R^3$ and Y are as defined above and A is as defined in the formula (I),
which compounds of formula (I) can be, if desired,
purified according to one or a number of purification methods chosen from crystallization, silica gel chromatography, extraction, filtration and passing through charcoal or resin,
separated, if appropriate, in the pure form or in the form of a mixture, into their possible enantiomers or diastereoisomers,
or salified by a pharmaceutically acceptable base.

The invention also relates to a process for the preparation of the compounds of formula (I), wherein a compound of formula (III):

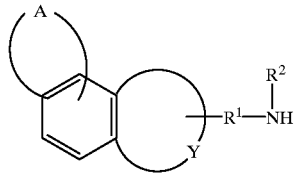

(III)

in which A, $R^1$, $R^2$ and Y are as defined in the formula (I), is reacted
a) with an acyl chloride of formula (IV):

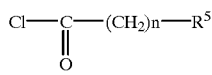

(IV)

in which n and $R^5$ are as defined in the formula (I), or with the corresponding acid anhydride (bis- or mixed-) or with formic acid,
b) or else with an isocyanate of formula (V):

$$X=C=N-(CH_2)_m-R^6$$ (V)

with X, m and $R^6$ as defined in the formula (I) in order to obtain, respectively:
a) the compound of formula (I/b1):

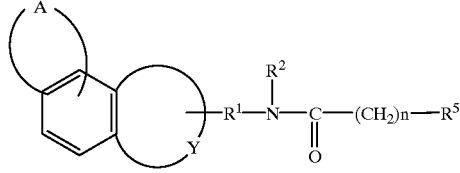

(I/b1)

in which A, Y, $R^1$, $R^2$, $R^5$ and n are as defined above,
or b) the compound of formula (I/b2):

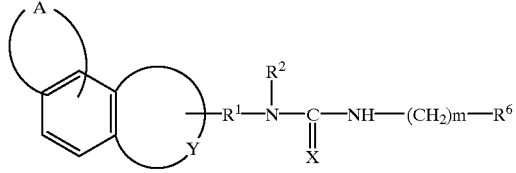

(I/b2)

in which A, Y, $R^1$, $R^2$, $R^6$, X and m are as defined above,
it being possible for the compounds of formula (I/b1) and (I/b2) to be, if desired,
purified according to one or a number of purification methods chosen from crystallization, silica gel chromatography, extraction, filtration and passing through charcoal or resin, separated, if appropriate, in the pure form or in the form of a mixture, into their possible enantiomers or diastereoisomers,
or salified by a pharmaceutically acceptable base.

The compound of formula (I) in which $R^{31}$ represents a $-CS-(CH_2)_n-R^5$ group can also be obtained from the corresponding compound of formula (I), in which $R^{31}$ represents a $-CO-(CH_2)_n-R^5$ group, which is subjected to a thionation reagent, for example Lawesson's reagent.

The invention also relates to the preparation of compounds of formula (I/c1):

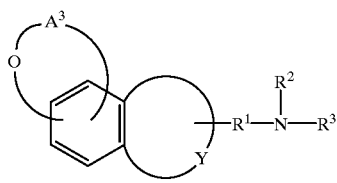

(I/c1)

in which $R^1$, $R^2$, $R^3$ and Y are as defined in the formula (I) and $A^3$ represents a $(C_2-C_5)$alkylene chain substituted by a hydroxyl radical or a $(C_2-C_5)$alkenylene chain, wherein the controlled reduction is carried out of a compound of formula (I/c0):

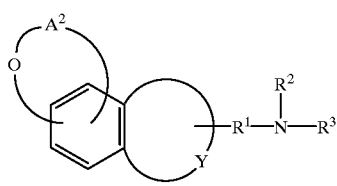

(I/c0)

in which $R^1$, $R^2$, $R^3$ and Y are as defined above and $A^2$ represents a $(C_2-C_5)$alkylene chain substituted by an oxo group,
it being possible for the compounds of formula (I/c1) to be, if desired,
purified according to one or a number of purification methods chosen from crystallization, silica gel chromatography, extraction, filtration and passing through charcoal or resin,
separated, if appropriate, in the pure form or in the form of a mixture, into their possible enantiomers or diastereoisomers,
or salified by a pharmaceutically acceptable base.

The invention also relates to a process for the preparation of the compounds of formula (I/d), a specific case of the compounds of formula (I):

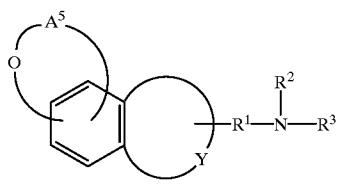

(I/d)

in which Y, $R^1$, $R^2$ and $R^3$ are as defined in the formula (I) and $A^5$ represents a $(C_2-C_5)$alkylene chain which is unsubstituted or substituted by a $(C_1-C_6)$alkyl radical, wherein a compound of formula (VI):

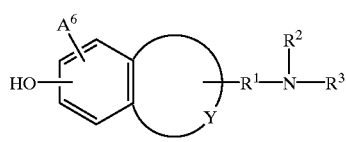

(VI)

in which Y, $R^1$, $R^2$ and $R^3$ are as defined above and $A^6$ represents a ($C_2$–$C_5$)alkenyl radical which is unsubstituted or substituted by a ($C_1$–$C_6$)alkyl radical, is subjected to a cyclization reaction, it being possible for the compounds of formula (I/d) to be, if desired, purified according to one or a number of purification methods chosen from crystallization, silica gel chromatography, extraction, filtration and passing through charcoal or resin, separated, if appropriate, in the pure form or in the form of a mixture, into their possible enantiomers or diastereoisomers, or salified by a pharmaceutically acceptable base.

The invention also relates to the compounds of formula (VI):

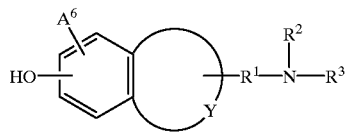

(VI)

in which $R^1$, $R^2$, $R^3$ and Y are as defined in the formula (I) and $A^6$ represents a ($C_2$–$C_5$)alkenyl radical which is unsubstituted or substituted by a ($C_1$–$C_6$)alkyl radical, which are useful as synthetic intermediates.

The compounds of formula (II) as described above are accessible to a person skilled in the art by reaction of a compound of formula (II/a):

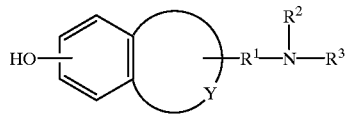

(II/a)

in which $R^1$, $R^2$, $R^3$ and Y are as defined in the formula (I), with a compound of formula (II/b):

$Z^2$—$A^1$—$Z^3$ (II/b)

in which $A^1$ has the same definition as in the formula (I), $Z^2$ represents an optionally protected reactive functional group and $Z^3$ represents a leaving group, for example a halogen atom or a tosyl group.

For example, $Z^2$ represents a hydroxyl or carboxyl functional group, a double bond or a triple bond.

The invention also applies to the compounds of formula (II):

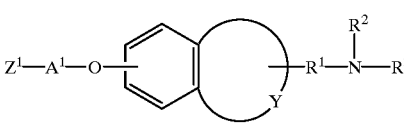

(II)

in which $R^1$, $R^2$, $R^3$ and $A^1$ are as defined in the formula (I) and $Z^1$ represents a reactive functional group, which are useful as synthetic intermediates.

The starting materials used in the processes described above are either commercially available or known in the state of the art or are easily accessible to a person skilled in the art according to processes which are well known in the literature. More specific reference will be made, for the compounds of general formula (II), to the descriptions of Patent EP 447,285 and of Patent Application EP 530,087.

The compounds of formula (I) have pharmacological properties which are of great interest the clinician.

The compounds of the invention and the pharmaceutical compositions containing them are proving to be useful in the treatment of disorders of the melatoninergic system.

The pharmacological study of the compounds of the invention has in fact shown that they were not toxic, that they had a very high selective affinity for melatonin receptors and that they had significant activities with respect to the central nervous system and, in particular, therapeutic properties with respect to sleep disorders, anxiolytic, antipsychotic and analgesic properties and properties with respect to the microcirculation were noted, which make it possible to establish that the products of the invention are useful in the treatment of stress, sleep disorders, anxiety, seasonal depressions, cardiovascular pathologies, insomnia and tiredness due to jet lag, schizophrenia, panic attacks, melancholia, eating disorders, obesity, insomnia, psychotic disorders, epilepsy, Parkinson's disease, senile dementia, various disorders related to normal or pathological ageing, migrane, memory losses, Alzheimer's disease and disorders of cerebral circulation. In another field of activity, it appears that the products of the invention have ovulation-inhibiting and immunomodulating properties and that they are capable of being used in anticancer treatment.

The compounds will preferably be used in the treatment of seasonal depressions, sleep disorders, cardiovascular pathologies, insomnia and tiredness due to jet lag, eating disorders and obesity.

For example, the compounds will be used in the treatment of seasonal depressions and sleep disorders.

Another subject of the present invention is the pharmaceutical compositions containing the products of formula (I) or, if appropriate, one of their addition salts with a pharmaceutically acceptable base in combination with one or a number of pharmaceutically acceptable excipients.

Mention can more particularly be made, among the pharmaceutical compositions according to the invention, of those which are suitable for oral, parenteral, nasal, per- or transcutaneous, rectal, perlingual, ocular or respiratory administration, may especially be mentioned, and in particular simple or sugar-coated tablets, sublingual tablets, chartulas, packets, gelatin capsules, glossettes, lozenges, suppositories, creams, ointments, dermal gels and imbibable or injectable phials.

The dosage varies according to the age and weight of the patient, the administration route, the nature of the therapeutic indication or possible associated treatments and ranges between 0.1 mg and 1 g per 24 hours in 1 or 2 administrations and more particularly 1 to 100 mg, for example 1 to 10 mg.

The following examples illustrate the invention but do not limit it in any way.

PREPARATION 1

N-{2-[7-(CARBOXYMETHYLOXY)NAPHTH-1-YL]ETHYL}ACETAMIDE

Stage A: N-{2-[7-(Ethoxycarbonylmethyloxy)naphth-1-yl]ethyl}acetamide

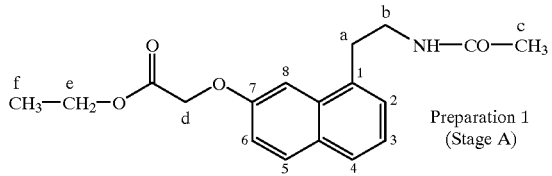

Preparation 1 (Stage A)

Reactants:
N-[2-(7-Hydroxynaphth-1-yl)ethyl]acetamide: 7 mmol (1.60 g)
Anhydrous acetone: 30 cm$^3$
Potassium carbonate: 14 mmol (1.93 g)
Ethyl bromoacetate: 10 mmol (1.67 g)

Procedure:

The N-[2-(7-hydroxynaphth-1-yl)ethyl]acetamide is dissolved in the anhydrous acetone, the potassium carbonate is added and the mixture is left stirring at reflux for a half-hour. The ethyl bromoacetate is added dropwise using a dropping funnel and the mixture is left stirring at reflux for three hours. The mixture is left to cool, the precipitate is filtered off, the filtrate is evaporated to dryness and the residue is recrystallized.

Characteristics:

Yield: 80%
Recrystallization solvent: toluene/hexane (1/2)
Melting point: 95–97° C.
Molecular mass: 315.355 g.mol$^{-1}$ for $C_{12}H_{21}NO_4$

| Microanalysis: | | | |
|---|---|---|---|
| | % C | % H | % N |
| Calculated: | 68.55 | 6.71 | 4.49 |
| Found: | 68.26 | 6.57 | 4.71 |

| Infrared: | | |
|---|---|---|
| 3300 | cm$^{-1}$ | ν N—H |
| 2960–2860 | cm$^{-1}$ | ν C—H alkyls |
| 1735 | cm$^{-1}$ | ν C=O ester |
| 1620 | cm$^{-1}$ | ν C=O amide |

NMR (d$_6$-DMSO) 300 MHz:

| 1.25 | ppm | triplet | 3H H$_f$, J$_{f-e}$ = 7.10 Hz |
|---|---|---|---|
| 1.85 | ppm | singlet | 3H H$_c$ |
| 3.15 | ppm | triplet | 2H H$_a$, J$_{a-b}$ = 6.80 Hz |
| 3.35 | ppm | multiplet | 2H H$_b$ |
| 4.20 | ppm | quartet | 2H H$_e$ |
| 5.00 | ppm | singlet | 2H H$_d$ |
| 7.20–7.35 | ppm | unresolved peak | 3H H$_2$, H$_3$, H$_6$ |
| 7.55 | ppm | doublet | 1H H$_8$, J$_{8-6}$ = 2.15 Hz |
| 7.75 | ppm | double doublet | 1H H$_4$, J$_{4-3}$ = 7.40 Hz, J$_{4-2}$ = 2.60 Hz |
| 7.85 | ppm | doublet | 1H H$_5$, J$_{5-6}$ = 9.00 Hz |
| 8.05 | ppm | triplet | 1H N—H amide |

Stage B: N-{2-[7-(Carboxymethyloxy)naphth-1-yl]ethyl}acetamide

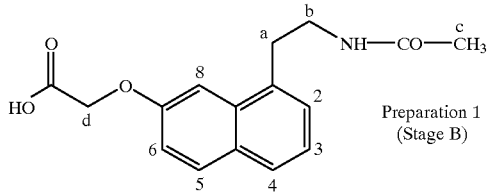

Preparation 1 (Stage B)

Reactants:

N-{2-[7-(Ethoxycarbonylmethyloxy)naphth-1-yl]ethyl}acetamide: 5 mmol (1.57 g)
10% Aqueous sodium hydroxide solution: 10 mmol (40 cm$^3$)

Procedure:

The N-[2-[7-(ethoxycarbonylmethyloxy)naphth-1-yl]ethyl]acetamide and a 10% aqueous sodium hydroxide solution are introduced into a flask and left to stir at room temperature until dissolution is complete. The reaction mixture is cooled in an ice bath and acidified with a concentrated hydrochloric acid solution. The precipitate is filtered off, washed with water, dried and recrystallized.

Characteristics:

Yield: 70%
Recrystallization solvent: alcohol/water (2/1)
Melting point: 181–184° C.
Molecular mass: 296.311 g.mol$^{-1}$ for $C_{16}H_{17}NO_4+0.5H_2O$

| Microanalysis: | | | |
|---|---|---|---|
| | % C | % H | % N |
| Calculated: | 64.85 | 6.12 | 4.72 |
| Found: | 64.84 | 5.77 | 4.87 |

| Infrared: | | |
|---|---|---|
| 3320 | cm$^{-1}$ | ν N—H amide |
| 2920–2860 | cm$^{-1}$ | ν C—H alkyls |
| 2500 | cm$^{-1}$ | ν CO$_2$H |
| 1700 | cm$^{-1}$ | ν C=O acide |
| 1610 | cm$^{-1}$ | ν C=O amide |

NMR (d$_6$-DMSO) 300 MHz:

| 1.80 ppm | singlet | 3H H$_c$ |
|---|---|---|
| 3.10 ppm | triplet | 2H H$_a$, J$_{a-b}$ = 7.15 Hz |
| 3.35 ppm | quartet | 2H H$_b$ |
| 4.90 ppm | singlet | 2H H$_d$ |
| 7.30 ppm | unresolved peak | 3H H$_2$, H$_3$, H$_6$ |
| 7.55 ppm | singlet | 1H H$_8$ |
| 7.80 ppm | doublet | 1H H$_4$, J$_{4-3}$ = 7.15 Hz |
| 7.90 ppm | doublet | 1H H$_5$, J$_{5-6}$ = 8.60 Hz |
| 8.10 ppm | signal | 1H N—H |
| 13.00 ppm | signal | 1H O—H, acidic, disappears with D$_2$O |

PREPARATION 2

N-{2-[7-(PROPARGYLOXY)NAPHTH-1-YL]ETHYL}ACETAMIDE

Preparation 2

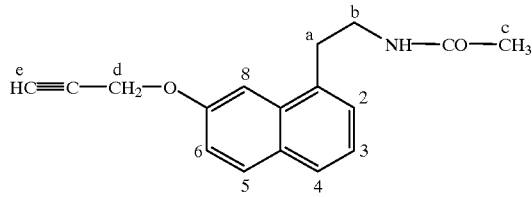

Reactants:

N-[2-(7-hydroxynaphth-1-yl)ethyl]acetamide: 5 mmol (1.15 g)
Sodium hydride: 18.75 mmol (0.45 g)
Tosylate of propargyl alcohol: 20 mmol
Dimethylformamide: 30 cm$^3$ Procedure:

The N-[2-(7-hydroxynaphth-1-yl)ethyl]acetamide and the dimethylformamide are introduced into a three-necked, round-bottomed flask, the sodium hydride is added in small portions and the reaction mixture is left stirring for two hours under nitrogen at room temperature. The tosylate of propargyl alcohol is added dropwise using a dropping funnel and the reaction mixture is left stirring for a half-hour under nitrogen. The reaction mixture is poured into water with stirring and extracted with ethyl acetate, the extract is washed with water, dried over calcium chloride, filtered and evaporated to dryness and the residue is recrystallized.

Characteristics:

Yield: 59%
Recrystallization solvent: hexane/toluene (2/1)
Melting point: 87–89° C.
Molecular mass: 267.313 g.mol$^{-1}$ for $C_{17}H_{17}NO_2$

| Microanalysis: | | | |
|---|---|---|---|
| | % C | % H | % N |
| Calculated: | 76.37 | 6.41 | 5.24 |
| Found: | 76.12 | 6.30 | 5.33 |

| Infrared: | | |
|---|---|---|
| 3270 | cm$^{-1}$ | ν N—H |
| 3200 | cm$^{-1}$ | ν C≡C—H |
| 2100 | cm$^{-1}$ | ν C≡C |
| 1620 | cm$^{-1}$ | ν C=O amide |

| NMR (d$_6$-DMSO) 300 MHz: | | | | |
|---|---|---|---|---|
| 1.85 | ppm | singlet | 3H | H$_c$ |
| 3.15 | ppm | triplet | 2H | H$_a$, J$_{a-b}$ = 6.70 Hz |
| 3.30 | ppm | multiplet | 2H | H$_b$ |
| 3.60 | ppm | singlet | 1H | H$_e$ |
| 5.00 | ppm | singlet | 2H | H$_d$ |
| 7.20–7.35 | ppm | unresolved peak | 3H | H$_2$, H$_3$, H$_6$ |
| 7.65 | ppm | singlet | 1H | H$_8$ |
| 7.75 | ppm | doublet | 1H | H$_4$, J$_{4-3}$ = 7.40 Hz |
| 7.85 | ppm | doublet | 1H | H$_5$, J$_{5-6}$ = 9.00 Hz |
| 8.05 | ppm | signal | 1H | NH amide |

By proceeding in an analogous way, the following preparations are obtained:

PREPARATION 3
N-{2-[7-(CARBOXYMETHYLOXY)NAPHTH-1-YL]ETHYL}-PROPIONAMIDE

PREPARATION 4
N-{2-[7-(CARBOXYMETHYLOXY)NAPHTH-1-YL]ETHYL}-BUTYRAMIDE

PREPARATION 5
N-{2-[7-(CARBOXYMETHYLOXY)NAPHTH-1-YL]ETHYL}-ISOBUTYRAMIDE

PREPARATION 6
N-{2-[7-(CARBOXYMETHYLOXY)NAPHTH-1-YL]ETHYL}-TRIFLUOROACETAMIDE

PREPARATION 7
N-{2-[7-(CARBOXYMETHYLOXY)NAPHTH-1-YL]ETHYL}FORMAMIDE

PREPARATION 8
N-{2-[7-(CARBOXYMETHYLOXY)NAPHTH-1-YL]ETHYL}PENTANAMIDE

PREPARATION 9
N-{2-[7-(CARBOXYMETHYLOXY)NAPHTH-1-YL]ETHYL}IODOACETAMIDE

PREPARATION 10
N-{2-[7-(CARBOXYMETHYLOXY)NAPHTH-1-YL]ETHYL}-CYCLOPROPANECARBOXAMIDE

PREPARATION 11
N-{2-[7-(CARBOXYMETHYLOXY)NAPHTH-1-YL]ETHYL}-CYCLOBUTANECARBOXAMIDE

PREPARATION 12
N-{2-[7-(CARBOXYMETHYLOXY)NAPHTH-1-YL]ETHYL}-CYCLOPENTANECARBOXAMIDE

PREPARATION 13
N-{2-[7-(CARBOXYMETHYLOXY)NAPHTH-1-YL]ETHYL}-CYCLOHEXANECARBOXAMIDE

PREPARATION 14
N-{2-[7-(CARBOXYMETHYLOXY)NAPHTH-1-YL]ETHYL}-PROPENE-1-CARBOXAMIDE

PREPARATION 15
N-{2-[7-(CARBOXYMETHYLOXY)NAPHTH-1-YL]ETHYL}-N'-METHYLUREA

PREPARATION 16
N-{2-[7-(CARBOXYMETHYLOXY)NAPHTH-1-YL]ETHYL}-N'-ETHYLUREA

PREPARATION 17
N-{2-[7-(CARBOXYMETHYLOXY)NAPHTH-1-YL]ETHYL}-N'-n-PROPYLUREA

PREPARATION 18
N-{2-[7-(CARBOXYMETHYLOXY)NAPHTH-1-YL]ETHYL}-N'-CYCLOPROPYLUREA

PREPARATION 19
N-{2-[7-(CARBOXYMETHYLOXY)NAPHTH-1-YL]ETHYL}N'-n-PROPYLTHIOUREA

PREPARATION 20
N-{2-[7-(CARBOXYMETHYLOXY)NAPHTH-1-YL]ETHYL}-N'-CYCLOPROPYLTHIOUREA

PREPARATION 21
N-{2-[7-(PROPARGYLOXY)NAPHTH-1-YL]ETHYL}-PROPIONAMIDE

PREPARATION 22
N-{2-[7-(PROPARGYLOXY)NAPHTH-1-YL]ETHYL}-BUTYRAMIDE

PREPARATION 23
N-{2-[7-(PROPARGYLOXY)NAPHTH-1-YL]ETHYL}-ISOBUTYRAMIDE

PREPARATION 24

N-{2-[7-(PROPARGYLOXY)NAPHTH-1-YL]ETHYL}TRIFLUOROACETAMIDE

PREPARATION 25

N-{2-[7-(PROPARGYLOXY)NAPHTH-1-YL]ETHYL}FORMAMIDE

PREPARATION 26

N-{2-[7-(PROPARGYLOXY)NAPHTH-1-YL]ETHYL}-PENTANAMIDE

PREPARATION 27

N-{2-[7-(PROPARGYLOXY)NAPHTH-1-YL]ETHYL}-IODOACETAMIDE

PREPARATION 28

N-{2-[7-(PROPARGYLOXY)NAPHTH-1-YL]ETHYL}CYCLOPROPANECARBOXAMIDE

PREPARATION 29

N-{2-[7-(PROPARGYLOXY)NAPHTH-1-YL]ETHYL}CYCLOBUTANECARBOXAMIDE

PREPARATION 30

N-{2-[7-(PROPARGYLOXY)NAPHTH-1-YL]ETHYL}CYCLOPENTANECARBOXAMIDE

PREPARATION 31

N-{2-[7-(PROPARGYLOXY)NAPHTH-1-YL]ETHYL}CYCLOHEXANECARBOXAMIDE

PREPARATION 32

N-{2-[7-(PROPARGYLOXY)NAPHTH-1-YL]ETHYL}PROPENE-1-CARBOXAMIDE

PREPARATION 33

N-{2-[7-(PROPARGYLOXY)NAPHTH-1-YL]ETHYL}-N'-METHYLUREA

PREPARATION 34

N-{2-[7-(PROPARGYLOXY)NAPHTH-1-YL]ETHYL}N'-ETHYLUREA

PREPARATION 35

N-{2-[7-(PROPARGYLOXY)NAPHTH-1-YL]ETHYL}-N'-PROPYLUREA

PREPARATION 36

N-{2-[7-(PROPARGYLOXY)NAPHTH-1-YL]ETHYL}-N'-CYCLOPROPYLUREA

PREPARATION 37

N-{2-[7-(PROPARGYLOXY)NAPHTH-1-YL]ETHYL}-N'-METHYLTHIOUREA

PREPARATION 38

N-{2-[7-(PROPARGYLOXY)NAPHTH-1-YL]ETHYL}-N'-CYCLOPROPYLTHIOUREA

PREPARATION 39

2-[7H-8,9-DIHYDROPYRANO[3,2-e]INDOLYL]ETHYLAMINE

This compound is described in J. Med. Chem., 1992, 35, p. 3625–3632.

PREPARATION 40

N-[2-(8-ALLYL-7-HYDROXYNAPHTH-1-YL)ETHYL]ACETAMIDE

Stage A: 2-(7-HYDROXYNAPHTH-1-YL)ETHYLAMINE HYDROBROMIDE

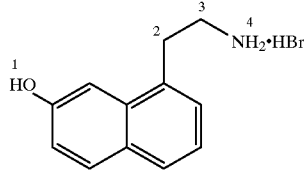

Stage A

Reactants:
2-(7-Methoxynaphth-1-yl)ethylamine hydrochloride: 58 mmol (13.8 g)
47% Aqueous HBr solution: 390 mmol (46 cm$^3$)

Procedure:
The ethylamine hydrochloride and the 47% HBr solution are introduced into a 250 cm$^3$ round-bottomed flask. The mixture is brought to reflux for 5 hours. After cooling, the reaction mixture is filtered.

Characteristics:
Molecular mass: 268.16 g for $C_{12}H_{14}BrNO$
Appearance: white solid
Melting point: 174–175° C.
$R_f$: 0.72 eluent: methanol/28% aqueous ammonia (4/1)
Yield: 80%
Recrystallization solvent: ethyl acetate/hexane (1/3)

| Infrared: | | |
|---|---|---|
| 3240–3460 | cm$^{-1}$ | ν OH |
| 3040–3100 | cm$^{-1}$ | ν C=C twisting |
| 2950–3060 | cm$^{-1}$ | ν CH |
| 2720–2480 | cm$^{-1}$ | ν NH$_3^+$ |

| NMR (d$_6$-DMSO, δ) 80 MHz: | | | | |
|---|---|---|---|---|
| 3.0–3.4 | ppm | unresolved peak | 4H | H$_2$, H$_3$ |
| 7.0–7.9 | ppm | unresolved peak | 6H | H, aromatic protons |
| 8.1 | ppm | singlet | 3H | H$_4$ |
| 9.8 | ppm | singlet | 1H | H$_1$ |

| Microanalysis: | | | |
|---|---|---|---|
| | % C | % H | % N |
| Calculated: | 53.75 | 5.26 | 5.22 |
| Found: | 53.84 | 5.30 | 5.32 |

Stage B: N-[2-(7-HYDROXYNAPHTH-1-YL)ETHYL]ACETAMIDE

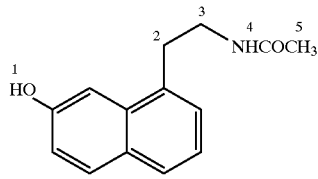

Stage B

Reactants:
2-(7-Hydroxynaphth-1-yl)ethylamine hydrobromide: 3.8 mmol (1.02 g)
Sodium carbonate: 8.5 mmol (0.90 g)

Acetyl chloride: 3.8 mmol (0.30 g)

Procedure:

The sodium carbonate is dissolved in 5 cm$^3$ of water in a 50 cm$^3$ flask and the hydrobromide is added with stirring. 20 cm$^3$ of ethyl acetate are added to the suspension obtained and then the acetyl chloride is run in dropwise. Stirring is maintained for 30 minutes (the solution is clear). The organic phase is extracted with water, then with a 1N aqueous HCl solution and then with water until the wash liquors are neutral. The organic phase is dried over magnesium sulfate, filtered and dried under reduced pressure.

Characteristics:

Molecular mass: 229.27 g for $C_{14}H_{15}BrNO_2$

Appearance: white solid

Melting point: 125–126° C.

$R_f$: 0.32 eluent: acetone/toluene/cyclohexane (4/4/2)

Yield: 60%

Recrystallization solvent: water

| Infrared: | | |
|---|---|---|
| 3340 | cm$^{-1}$ | ν OH |
| 2980 | cm$^{-1}$ | ν CH |
| 1460 | cm$^{-1}$ | ν CH$_3$ |
| 1640 | cm$^{-1}$ | ν CO amide |

| NMR (CDCl$_3$, δ) 80 MHz: | | | | |
|---|---|---|---|---|
| 2.0 | ppm | singlet | 3H | H$_5$ |
| 3.2 | ppm | triplet | 2H | H$_2$, J$_{2-3}$ =7.1 Hz |
| 3.6 | ppm | quintet | 2H | H$_3$, J$_{3-2}$ = 7.1 Hz, J$_{3-4}$ = 7.1 Hz |
| 5.8 | ppm | signal | 1H | H4 |
| 7.0–7.9 | ppm | unresolved peak | 6H | H, aromatic protons |
| 9.5 | ppm | singlet | 1H | H1 |

| Microanalysis: | | | |
|---|---|---|---|
|  | % C | % H | % N |
| Calculated: | 73.34 | 6.59 | 6.11 |
| Found: | 72.99 | 6.57 | 6.29 |

Stage C: N-[2-(7-ALLYLOXYNAPHTH-1-YL)ETHYL]ACETAMIDE

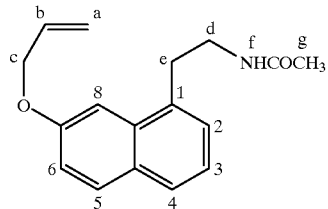

Stage C

Reactants:

N-[2-(7-Hydroxynaphth-1-yl)ethyl]acetamide: 20 mmol (5 g)

Sodium carbonate: 50 mmol (6.63 g)

Allyl bromide: 30 mmol (3.63 g)

Procedure:

The compound obtained in the preceding stage is dissolved in 100 cm$^3$ of anhydrous acetone. The sodium carbonate is added and the reaction mixture is left stirring at reflux for 30 minutes. The allyl bromide is added dropwise. The reaction mixture is left at reflux and with stirring for 3 hours. After cooling, the reaction mixture is filtered and the filtrate is dried under reduced pressure. The oil obtained is purified by column chromatography.

Characteristics:

Molecular mass: 269.33 g for $C_{17}H_{19}NO_2$

Appearance: oil $R_f$: 0.19 eluent: acetone/toluene/cyclohexane (2/3/5)

Yield: 87%

| Infrared: | | |
|---|---|---|
| 3260 | cm$^{-1}$ | ν NH amide |
| 2920–2840 | cm$^{-1}$ | ν CH |
| 1635 | cm$^{-1}$ | ν CO amide |
| 1590 | cm$^{-1}$ | ν C=C |

| NMR (CDCl$_3$, δ) 300 MHz: | | | | |
|---|---|---|---|---|
| 1.90 | ppm | singlet | 3H | H$_g$ |
| 3.20 | ppm | triplet | 2H | H$_e$ | J$_{e-d}$ = 7.00 Hz |
| 3.60 | ppm | quintet | 2H | H$_d$ |
| 4.70 | ppm | doublet | 2H | H$_c$ | J$_{c-b}$ = 5.28 Hz |
| 5.30 | ppm | doublet | 1H | H$_a$ cis, | J$_{a-b}$ = 10.46 Hz |
| 5.50 | ppm | doublet | 1H | H$_a$ trans, | J$_{a-b}$ = 17.30 Hz |
| 5.60 | ppm | signal | 1H | H$_f$ |
| 6.15 | ppm | multiplet | 1H | H$_b$ |
| 7.15 | ppm | double doublet | 1H | H$_6$ | J$_{ortho}$ = 8.90, J$_{meta}$ = 2.30 |
| 7.25 | ppm | multiplet | 2H | H$_{2,3}$ |
| 7.40 | ppm | doublet | 1H | H$_8$ |
| 7.65 | ppm | multiplet | 1H | H$_3$ |
| 7.75 | ppm | doublet | 1H | H$_5$ | J$_{ortho}$ = 8.30 |

| Microanalysis: | | | |
|---|---|---|---|
|  | % C | % H | % N |
| Calculated: | 75.80 | 7.11 | 5.20 |
| Found: | 75.75 | 7.15 | 5.20 |

Stage D: N-[2-(8-ALLYL-7-HYDROXYNAPHTH-1-YL)ETHYL]ACETAMIDE

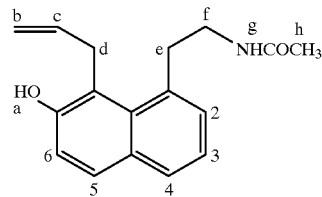

Stage D

Reactants:

N-[2-(7-Allyloxynaphth-1-yl)ethyl]acetamide: 7.4 mmol (2 g)

N,N-Dimethylaniline: 7.4 mmol (10 cm$^3$)

Procedure:

The N-[2-(7-allyloxynaphth-1-yl)ethyl]acetamide is dissolved in the N,N-dimethylaniline and the reaction mixture is brought to reflux (200° C.) for 2 hours. After cooling, 20 cm$^3$ of ether are added and the organic phase is extracted with a 10% aqueous sodium hydroxide solution and then with water. The aqueous phase is then acidified with a 6N aqueous HCl solution and left stirring for a few minutes. The precipitate obtained is filtered.

Characteristics:

Molecular mass: 269.33 g.mol$^{-1}$ for $C_{17}H_{19}NO_2$

Appearance: pale yellow solid $R_f$: 0.38 eluent: acetone/toluene/cyclohexane (4/4/2)

Melting point: 157–159° C.

Yield: 84%

Recrystallization solvent: cyclohexane

| Infrared: | | |
|---|---|---|
| 3280 | cm$^{-1}$ | ν NH amide |
| 2860–3000 | cm$^{-1}$ | ν CH |
| 1600 | cm$^{-1}$ | ν CO amide |

| NMR (d$_6$-DMSO, δ) 300 MHz: | | | | |
|---|---|---|---|---|
| 1.83 | ppm | singlet | 3H | H$_h$ |
| 3.20 | ppm | signal | 2H | H$_e$ |
| 3.25 | ppm | signal | 2H | H$_f$ |
| 3.90 | ppm | signal | 2H | H$_d$ |
| 4.65 | ppm | doublet | 1H | H$_b$ trans, J$_{b-c}$ = 17.2 Hz |
| 4.95 | ppm | doublet | 1H | H$_b$ cis, J$_{b-c}$ = 8.8 Hz |
| 6.05 | ppm | multiplet | 1H | H$_c$ |
| 7.17 | ppm | signal | 1H | H$_6$ |
| 7.18 | ppm | signal | 1H | H$_3$, J$_{3-2}$ = 7.4 Hz, J$_{3-4}$ = 4.33 Hz |
| 7.21 | ppm | signal | 1H | H$_2$, J$_{2-3}$ = 7.5 Hz |
| 7.65 | ppm | signal | 1H | H$_4$, J$_{4-3}$ = 7.4 Hz |
| 7.67 | ppm | signal | 1H | H$_5$, J$_{5-6}$ = 8.6 Hz |
| 8.08 | ppm | signal | 1H | H$_g$ |
| 9.60 | ppm | singlet | 1H | H$_a$, exchangeable in D$_2$O |

PREPARATION 41

N-[2-(8-ALLYL-7-HYDROXYNAPHTH-1-YL)ETHYL]-N'-METHYLUREA

EXAMPLE 1

2,3-DIHYDRO-3-OXO-4-(2-ACETAMIDOETHYL)-1-NAPHTHO[2,1-b]-FURAN

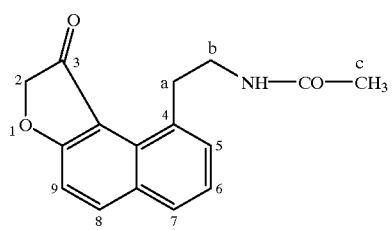

Example 1

Reactants:
N-(2-[7-(Carboxymethyloxy)naphth-1-yl]ethyl)acetamide (Preparation 1): 10 mmol (2.9 g)
Polyphosphoric acid: 30 g
Procedure:
The N-{2-[7-(carboxymethyloxy)naphth-1-yl]ethyl}acetamide and the polyphosphoric acid are introduced into a 100 cm$^3$ round-bottomed flask with a ground-glass neck and the reaction mixture is stirred using a mechanical stirrer at 85° C. for two hours and a half. The reaction mixture is left stirring for one hour and is poured into ice-old water. Extraction is carried out with ethyl acetate and the organic phase is washed twice with a 10% aqueous sodium carbonate solution, then washed with water, dried over calcium chloride, filtered and evaporated to dryness. The product is purified on a column with 60 Å silica gel, using the acetone/toluene (1/1) eluent.
Characteristics:
Yield: 32%
Recrystallization solvent: hexane/toluene (2/1)
Melting point: 157–158° C.

Molecular mass: 269.287 g.mol$^{-1}$ for C$_{16}$H$_{15}$NO$_3$

| Microanalysis: | | | |
|---|---|---|---|
| | % C | % H | % N |
| Calculated: | 71.35 | 5.61 | 5.20 |
| Found: | 71.33 | 5.46 | 5.17 |

| Infrared: | | |
|---|---|---|
| 3270 | cm$^{-1}$ | ν N—H amide |
| 2920–2860 | cm$^{-1}$ | ν C—H alkyl |
| 1685 | cm$^{-1}$ | ν C=O ketone |
| 1610 | cm$^{-1}$ | ν C=O amide |

| NMR (d$_6$-DMSO) 300 MHz: | | | | |
|---|---|---|---|---|
| 1.75 | ppm | singlet | 3H | H$_c$ |
| 3.25 | ppm | quartet | 2H | H$_b$ |
| 3.60 | ppm | triplet | 2H | H$_a$, J$_{a-b}$ = 6.60 Hz |
| 7.45 | ppm | unresolved peak | 3H | H$_5$, H$_6$, H$_9$ |
| 7.75 | ppm | signal | 1H | N—H |
| 7.85 | ppm | doublet | 1H | H$_7$, J$_{7-6}$ = 7.40 Hz |
| 8.30 | ppm | doublet | 1H | H$_8$, J$_{8-9}$ = 9.00 Hz |

EXAMPLE 2

2,3-DIHYDRO-3-HYDROXY-(2-ACETAMIDOETHYL)-1-NAPHTHO-[2,1-b]FURAN

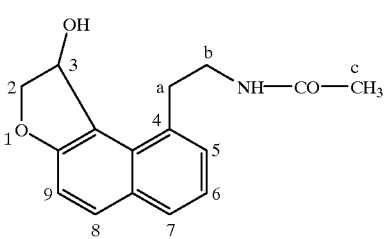

Example 2

Reactants:
2,3-Dihydro-3-oxo-4-(2-acetamidoethyl)-1-naphtho[2,1-b] furan (Example 1): 5 mmol (1.35 g)
Methanol: 30 cm$^3$
Sodium borohydride: 10 mmol (0.32 g)
Procedure:
The 2,3-dihydro-3-oxo-4-(2-acetamidoethyl)-1-naphtho[2,1-b]furan and the methanol are introduced into a 100 cm$^3$ flask with a ground-glass neck, the sodium borohydride (5 mmol) is added in small portions and the reaction mixture is left stirring. After two hours, sodium borohydride (5 mmol) is added in small portions and the reaction mixture is left to stir overnight at room temperature. The reaction mixture is evaporated to dryness and the residue is taken up in water and acidified with a 6N hydrochloric acid solution. The precipitate is filtered off, washed with water until the wash liquors are neutral, dried and recrystallized from toluene.
Characteristics:
Yield: 51%
Melting point: 153–156° C.

Molecular mass: 271.303 g.mol$^{-1}$ for $C_{16}H_{17}NO_3$

| Microanalysis: | | | |
|---|---|---|---|
| | % C | % H | % N |
| Calculated: | 70.82 | 6.31 | 5.16 |
| Found: | 70.61 | 6.28 | 5.04 |

| Infrared: | | |
|---|---|---|
| 3250 | cm$^{-1}$ | ν O—H and N—H |
| 1620 | cm$^{-1}$ | ν C=O amide |

| NMR (d$_6$-DMSO) 300 MHz: | | | | |
|---|---|---|---|---|
| 1.80 | ppm | singlet | 3H | H$_c$ |
| 3.00–3.65 | ppm | unresolved peak | 4H | H$_a$, H$_b$ |
| 4.50 | ppm | multiplet | 2H | H$_2$ |
| 5.60 | ppm | doublet | 1H | OH, disappears with D$_2$O, J = 7.00 |
| 5.70 | ppm | multiplet | 1H | H$_3$ |
| 7.20–7.35 | ppm | unresolved peak | 3H | H$_5$, H$_6$, H$_9$ |
| 7.75 | ppm | doublet | 1H | H$_7$, J$_{7-6}$ = 7.85 Hz |
| 7.90 | ppm | doublet | 1H | H$_8$, J$_{8-9}$ = 8.80 Hz |
| 8.05 | ppm | signal | 1H | N—H amide |

EXAMPLE 3

4-(2-ACETAMIDOETHYL)-1-NAPHTHO[2,1-b]FURAN

Example 3

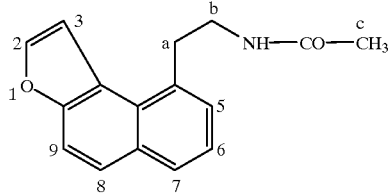

Reactants:

2,3-Dihydro-3-oxo-4-(2-acetamidoethyl)-1-naphtho[2, 1-b]furan (Example 1): 5 mmol (1.38 g)
Methanol: 30 cm$^3$
Sodium borohydride: 20 mmol (0.76 g)

Procedure:

The 2,3-dihydro-3-oxo-4-(2-acetamidoethyl)-1-naphtho[2,1-b]furan and the methanol are introduced into a 100 cm$^3$ round-bottomed flask and 10 mmol of sodium borohydride are added in small portions with stirring.

After two hours, sodium borohydride (10 mmol) is added in small portions with stirring. The reaction mixture is left stirring at room temperature and acidified with a 6N hydrochloric acid solution, the methanol is evaporated, the residue is taken up in water and the precipitate is filtered off, washed with water until the wash liquors are neutral, dried and recrystallized from toluene/hexane.

Yield: 85%
Melting point: 142–144° C.
Molecular mass: 253.287 g.mol$^{-1}$ for $C_{16}H_{15}NO_2$

| Microanalysis: | | | |
|---|---|---|---|
| | % C | % H | % N |
| Calculated: | 75.80 | 5.96 | 5.53 |
| Found: | 75.57 | 5.97 | 5.47 |

| Infrared: | | |
|---|---|---|
| 3240 | cm$^{-1}$ | ν N—H amide |
| 1625 | cm$^{-1}$ | ν C=O amide |

| NMR (d$_6$-DMSO) 300 MHz: | | | | |
|---|---|---|---|---|
| 1.85 | ppm | singlet | 3H | H$_c$ |
| 3.40 | ppm | multiplet | 4H | H$_a$, H$_b$ |
| 7.50 | ppm | multiplet | 2H | H$_3$, H$_9$ |
| 7.80–7.95 | ppm | unresolved peak | 4H | H$_5$, H$_6$, H$_7$, H$_8$ |
| 8.20 | ppm | multiplet | 2H | H$_2$, NH |

EXAMPLE 4

5-(2-ACETAMIDOETHYL)-2H-1-NAPHTHO[2,1-b]PYRAN

Example 4

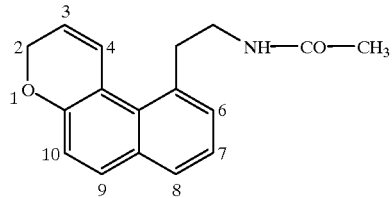

Reactants:

N-{2-[7-(Propargyloxy)naphth-1-yl]ethyl}acetamide (Preparation 2): 10 mmol (2.67 g)
Triethylene glycol: 40 cm$^3$ Procedure:

The N-{2-[7-(propargyloxy)naphth-1-yl]ethyl}acetamide and the triethylene glycol are introduced into a two-necked, round-bottomed flask. The reaction mixture is heated at 160°–170° C. under nitrogen and with stirring for five hours. The reaction mixture is poured into ice-cold water and extracted with ethyl acetate and the extract is washed with water, dried over calcium chloride, filtered and evaporated to dryness.

The product is purified on a 60 Å silica column with an acetone/toluene (1/1) eluent.

Characteristics:

Yield: 23%
Recrystallization solvent: toluene/hexane
Melting point: decomposes at 113° C.
Molecular mass: 267.313 g.mol$^{-1}$ for $C_{17}H_{17}NO_2$

| Microanalysis: | | | |
|---|---|---|---|
| | % C | % H | % N |
| Calculated: | 76.37 | 6.41 | 5.24 |
| Found: | 76.16 | 6.40 | 5.52 |

-continued

| Infrared: | | |
|---|---|---|
| 3250 | cm$^{-1}$ | ν N—H |
| 2960–2840 | cm$^{-1}$ | ν C—H alkyls |
| 1630 | cm$^{-1}$ | ν C=O amide |

| NMR (d$_6$-DMSO) 300 MHz: | | | | |
|---|---|---|---|---|
| 1.80 | ppm | singlet | 3H | H$_c$ |
| 3.20 | ppm | triplet | 2H | H$_a$, J$_{a-b}$ = 6.80 Hz |
| 3.40 | ppm | multiplet | 2H | H$_b$ |
| 4.65 | ppm | doublet | 2H | H$_2$, J$_{2-3}$ = 4.30 Hz |
| 5.90 | ppm | multiplet | 1H | H$_3$ |
| 7.10 | ppm | doublet | 1H | H$_4$, J$_{4-3}$ = 8.80 Hz |
| 7.30 | ppm | unresolved peak | 3H | H$_6$, H$_7$, H$_{10}$ |
| 7.70 | ppm | doublet | 1H | H$_8$, J$_{8-7}$ = 7.50 Hz |
| 7.80 | ppm | doublet | 1H | H$_9$, J$_{9-10}$ = 9.80 Hz |
| 8.10 | ppm | signal | 1H | N—H amide |

EXAMPLE 5

3,4,5,6,7,8-HEXAHYDRO-5-(2-ACETAMIDOETHYL)-2H-1-NAPHTHO-[2,1-b]PYRAN

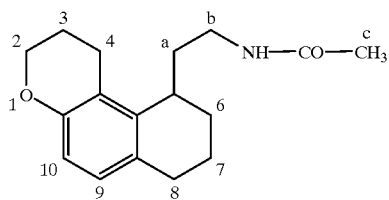

Example 5

Reactants:
5-(2-Acetamidoethyl)-2H-1-naphtho[2,1-b]pyran (Example 4): 2 mmol (5.34 mg)
Methanol: 25 cm$^3$
Raney nickel: a few mg
Procedure:
The 5-(2-acetamidoethyl)-2H-1-naphtho[2,1-b]pyran is dissolved in the methanol, the Raney nickel is added and the reaction mixture is stirred under a hydrogen atmosphere at ordinary pressure at room temperature for six hours. The reaction mixture is filtered. The filtrate is evaporated to dryness and the residue is recrystallized.
Characteristics:
Yield: 55%
Recrystallization solvent: toluene
Melting point: 117–118° C.
Molecular mass: 273.361 g.mol$^{-1}$ for C$_{17}$H$_{23}$NO$_2$

| Microanalysis: | % C | % H | % N |
|---|---|---|---|
| Calculated | 74.68 | 8.48 | 5.12 |
| Found | 74.46 | 8.39 | 5.16 |

| Infrared: | | |
|---|---|---|
| 3240 | cm$^{-1}$ | ν N—H amide |
| 2980-2800 | cm$^{-1}$ | ν C—H alkyls |
| 1610 | cm$^{-1}$ | ν C=O amide |

| NMR (d$_6$-DMSO) 80 MHz: | | | | |
|---|---|---|---|---|
| 1.30–2.15 | ppm | unresolved peak | 11H | H$_a$, H$_c$, H$_3$, H$_6$, H$_7$ |
| 2.35–2.80 | ppm | unresolved peak | 5H | H$_4$, H$_5$, H$_8$ |
| 3.20 | ppm | multiplet | 2H | H$_b$ |
| 4.00 | ppm | multiplet | 2H | H$_2$ |
| 6.50 | ppm | doublet | 1H | H$_{10}$, J$_{10-9}$ = 9.20 Hz |
| 6.75 | ppm | doublet | 1H | H$_9$, J$_{9-10}$ = 9.20 Hz |
| 7.90 | ppm | signal | 1H | N—H amide |

EXAMPLE 6

3,4-DIHYDRO-5-(2-ACETAMIDOETHYL)-2H-1-NAPHTHO[2,1-b]PYRAN

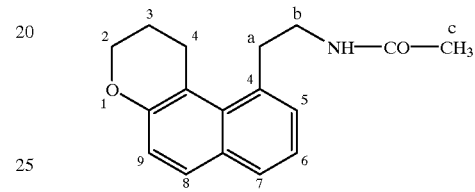

Example 6

Reactants:
5-(2-Acetamidoethyl)-2H-1-naphtho[2,1-b]pyran (Example 4): 2 mmol (534 mg)
Methanol: 80 cm$^3$
Magnesium: 80 mmol (1.35 g)
Procedure:
The 5-(2-acetamidoethyl)-2H-1-naphtho[2,1-b]pyran is dissolved in the methanol and the reaction mixture is cooled using an ice/salt bath. The magnesium is added in small portions and the reaction mixture is left stirring at room temperature for 16 hours. 30 cm$^3$ of a 6N hydrochloric acid solution are added little by little, with stirring. The reaction mixture is left to cool, is extracted with ether and the organic phase is washed with water, dried over magnesium sulfate, filtered and evaporated to dryness.
Characteristics:
Yield: 42%
Recrystallization solvent: ether/petroleum ether
Melting point: 137–139° C.
Molecular mass: 291.849 g.mol$^{-1}$ for C$_{17}$H$_{19}$NO$_2$+1.25H$_2$O

| Microanalysis: | % C | % H | % N |
|---|---|---|---|
| Calculated | 69.95 | 6.99 | 4.79 |
| Found | 70.00 | 6.63 | 4.75 |

| Infrared: | | |
|---|---|---|
| 3240 | cm$^{-1}$ | ν N—H amide |
| 2980-2800 | cm$^{-1}$ | ν C—H alkyls |
| 1610 | cm$^{-1}$ | ν C=O amide |

| NMR (d$_6$-DMSO) 300 MHz: | | | | |
|---|---|---|---|---|
| 1.50–2.10 | ppm | unresolved peak | 5H | H$_3$, H$_c$ |
| 3.10–3.85 | ppm | unresolved peak | 6H | H$_a$, H$_b$, H$_4$ |
| 3.95 | ppm | multiplet | 2H | H$_2$ |
| 7.15–7.30 | ppm | unresolved peak | 3H | H$_6$, H$_7$, H$_{10}$ |
| 7.65 | ppm | doublet | 1H | H$_8$, J$_{8-7}$ = 7.45 Hz |
| 7.80 | ppm | doublet | 1H | H$_9$, J$_{9-10}$ = 9.90 Hz |
| 8.10 | ppm | signal | 1H | N—H |

EXAMPLES 7 TO 114

By proceeding as in Examples 1 to 6, but by using the appropriate preparations, the compounds of the following examples are obtained.

EXAMPLE 7
2,3-DIHYDRO-3-OXO-4-(2-PROPIONAMIDOETHYL)-1-NAPHTHO[2,1-b]-FURAN

EXAMPLE 8
2,3-DIHYDRO-3-OXO-4-(2-BUTYRAMIDOETHYL)-1-NAPHTHO[2,1-b]-FURAN

EXAMPLE 9
2,3-DIHYDRO-3-OXO-4-(2-ISOBUTYRAMIDOETHYL)-1-NAPHTHO[2,1-b]-FURAN

EXAMPLE 10
2,3-DIHYDRO-3-OXO-4-(2-TRIFLUOROACETAMIDOETHYL)-1-NAPHTHO[2,1-b]FURAN

EXAMPLE 11
2,3-DIHYDRO-3-OXO-4-(2-FORMAMIDOETHYL)-1-NAPHTHO[2,1-b]-FURAN

EXAMPLE 12
2,3-DIHYDRO-3-OXO-4-(2-PENTANAMIDOETHYL)-1-NAPHTHO[2,1-b]-FURAN

EXAMPLE 13
2,3-DIHYDRO-3-OXO-4-[2(IODOACETAMIDO)ETHYL]-1-NAPHTHO-[2,1-b]FURAN

EXAMPLE 14
2,3-DIHYDRO-3-OXO-4-[2-(CYCLOPROPANECARBOXAMIDO)ETHYL]-1-NAPHTHO[2,1-b]FURAN

EXAMPLE 15
2,3-DIHYDRO-3-OXO-4-[2-(CYCLOBUTANECARBOXAMIDO)ETHYL-]1-NAPHTHO[2,1-b]FURAN

EXAMPLE 16
2,3-DIHYDRO-3-OXO-4-[2-(CYCLOPENTANECARBOXAMIDO)ETHYL]-1-NAPHTHO[2,1-b]FURAN

EXAMPLE 17
2,3-DIHYDRO-3-OXO-4-[2-(CYCLOHEXANECARBOXAMIDO)ETHYL]-1-NAPHTHO[2,1-b]FURAN

EXAMPLE 18
2,3-DIHYDRO-3-OXO-4-[2-(PROPENE-1-CARBOXAMIDO)ETHYL]-1-NAPHTHO[2,1-b]FURAN

EXAMPLE 19
2,3-DIHYDRO-3-HYDROXY-4-(2-PROPIONAMIDOETHYL)-1-NAPHTHO-[2,1-b]FURAN

EXAMPLE 20
2,3-DIHYDRO-3-HYDROXY-(2-BUTYRAMIDOETHYL)-1-NAPHTHO-[2,1-b]FURAN

EXAMPLE 21
2,3-DIHYDRO-3-HYDROXY-4-(2-ISOBUTYRAMIDOETHYL)-1-NAPHTHO[2,1-b]FURAN

EXAMPLE 22
2,3-DIHYDRO-3-HYDROXY 4(2-TRIFLUOROACETAMIDOETHYL)-1-NAPHTHO[2,1-b]FURAN

EXAMPLE 23
2,3-DIHYDRO-3-HYDROXY 4(2-FORMAMIDOETHYL)-1-NAPHTHO-[2,1-b]FURAN

EXAMPLE 24
2,3-DIHYDRO-3-HYDROXY-4(2-PENTANAMIDOETHYL)-1-NAPHTHO-[2,1-b]FURAN

EXAMPLE 25
2,3-DIHYDRO-3-HYDROXY-4-[2-(IODOACETAMIDO)ETHYL]-1-NAPHTHO[2,1-b]FURAN

EXAMPLE 26
2,3-DIHYDRO-3-HYDROXY-4-[2-(CYCLOPROPANECARBOXAMIDO) ETHYL]-1-NAPHTHO[2,1-b]FURAN

EXAMPLE 27
2,3-DIHYDRO-3-HYDROXY-4-[2-(CYCLOBUTANECARBOXAMIDO) ETHYL]-1-NAPHTHO[2,1-b]FURAN

EXAMPLE 28
2,3-DIHYDRO-3-HYDROXY-4-[2-(CYCLOPENTANECARBOXAMIDO) ETHYL]-1-NAPHTHO[2,1-b]FURAN

EXAMPLE 29
2,3-DIHYDRO-3-HYDROXY-4-[2-(CYCLOHEXANECARBOXAMIDO)ETHYL]-1-NAPHTHO[2,1-b]FURAN

EXAMPLE 30
2,3-DIHYDRO-3-HYDROXY-[2-(PROPENE-1-CARBOXAMIDO)ETHYL]-1-NAPHTHO[2,1-b]FURAN

EXAMPLE 31
4-(2-PROPIONAMIDOETHYL)-1-NAPHTHO[2,1-b]FURAN

EXAMPLE 32
4-(2-BUTYRAMIDOETHYL)-1-NAPHTHO[2,1-b]FURAN

EXAMPLE 33
4-(2-ISOBUTYRAMIDOETHYL)1-NAPHTHO[2,1-b]FURAN

EXAMPLE 34
4-(2-TRIFLUOROACETAMIDOETHYL)-1-NAPHTHO[2,1-b]FURAN

EXAMPLE 35
4-(2-FORMAMIDOETHYL)-1-NAPHTHO[2,1-b]FURAN

EXAMPLE 36
4-(2-PENTANAMIDOETHYL)-1-NAPHTHO[2,1-b]FURAN

EXAMPLE 37
4-[2-(IODOACETAMIDO)ETHYL]-1-NAPHTHO[2,1-b]FURAN

EXAMPLE 38
4-[2-(CYCLOPROPANECARBOXAMIDO)ETHYL-]1-NAPHTHO[2,1-b]-FURAN

EXAMPLE 39
4-[2-(CYCLOBUTANECARBOXAMIDO)ETHYL]-1-NAPHTHO[2,1-b]-FURAN

EXAMPLE 40
4-[2-(CYCLOPENTANECARBOXAMIDO)ETHYL]-1-NAPHTHO[2,1-b]-FURAN

EXAMPLE 41
4-[2-(CYCLOHEXANECARBOXAMIDO)ETHYL]-1-NAPHTHO[2,1-b]-FURAN

EXAMPLE 42
4-[2-(PROPENE-1-CARBOXAMIDO)ETHYL]-1-NAPHTHO[2,1-b]FURAN

EXAMPLE 43
5-(2-PROPIONAMIDOETHYL)-2H-1-NAPHTHO[2,1-b]PYRAN

EXAMPLE 44
5-(2-BUTYRAMIDOETHYL)-2H-1-NAPHTHO[2,1-b]PYRAN

EXAMPLE 45
5-(2-ISOBUTYRAMIDOETHYL)-2H-1-NAPHTHO[2,1-b]PYRAN

EXAMPLE 46
5-(2-TRIFLUOROACETAMIDOETHYL)-2H-1-NAPHTHO[2,1-b]PYRAN

EXAMPLE 47:
5-(2-FORMAMIDOETHYL)-2H-1-NAPHTHO[2,1-b]PYRAN

EXAMPLE 48
5-(2-PENTANAMIDOETHYL)-2H-1-NAPHTHO[2,1-b]PYRAN

EXAMPLE 49
5-[2(IODOACETAMIDO)ETHYL]-2H-1-NAPHTHO[2,1-b]PYRAN

EXAMPLE 50
5-[2-(CYCLOPROPANECARBOXAMIDO)ETHYL]-2H-1-NAPHTHO-[2,1-b]PYRAN

EXAMPLE 51
5-[2-(CYCLOBUTANECARBOXAMIDO)ETHYL]-2H-1-NAPHTHO[2,1-b]-PYRAN

EXAMPLE 52
5-[2-(CYCLOPENTANECARBOXAMIDO)ETHYL]-2H-1-NAPHTHO[2,1-b]-PYRAN

EXAMPLE 53
5-[2-(CYCLOHEXANECARBOXAMIDO)ETHYL]-2H-1-NAPHTHO[2,1-b]-PYRAN

EXAMPLE 54
5-[2-(PROPENE-1-CARBOXAMIDO)ETHYL]-2H-1-NAPHTHO[2, 1-b]-PYRAN

EXAMPLE 55
3,4,5,6,7,8-HEXAHYDRO-5-(2-PROPIONAMIDOETHYL)-2H-1 NAPHTHO[2,1-b]PYRAN

EXAMPLE 56
3,4,5,6,7,8-HEXAHYDRO-5-(2-BUTYRAMIDOETHYL)-2H-1-NAPHTHO-[2,1-b]PYRAN

EXAMPLE 57
3,4,5,6,7,8-HEXAHYDRO-5-(2-ISOBUTYRAMIDOETHYL)-2H-1 NAPHTHO[2,1-b]PYRAN

EXAMPLE 58
3,4,5,6,7,8-HEXAHYDRO-5-(2-TRIFLUOROACETAMIDOETHYL)-2H-1-NAPHTHO[2,1-b]PYRAN

EXAMPLE 59
3,4,5,6,7,8-HEXAHYDRO-5-(2-FORMAMIDOETHYL)-2H-1-NAPHTHO-[2,1-b]PYRAN

EXAMPLE 60
3,4,5,6,7,8-HEXAHYDRO-5-(2-PENTANAMIDOETHYL)-2H-1-NAPHTHO-[2,1-b]PYRAN

EXAMPLE 61
3,4,5,6,7,8-HEXAHYDRO-5-[2-(IODOACETAMIDO)ETHYL]-2H-1-NAPHTHO[2,1-b]PYRAN

EXAMPLE 62
3,4,5,6,7,8-HEXAHYDRO-5-[2-(CYCLOPROPANECARBOXAMIDO)ETHYL]-2H-1-NAPHTHO[2,1-b]PYRAN

EXAMPLE 63
3,4,5,6,7,8-HEXAHYDRO-5-[2-(CYCLOBUTANECARBOXAMIDO)ETHYL]-2H-1-NAPHTHO[2,1-b]PYRAN

EXAMPLE 64
3,4,5,6,7,8-HEXAHYDRO-5-[2-(CYCLOPENTANECARBOXAMIDO)ETHYL]-2H-1-NAPHTHO[2,1-b]PYRAN

EXAMPLE 65
3,4,5,6,7,8-HEXAHYDRO-5-[2-(CYCLOHEXANECARBOXAMIDO)ETHYL]-2H-1-NAPHTHO[2,1-b]PYRAN

EXAMPLE 66
3,4,5,6,7,8-HEXAHYDRO-5-[2-(PROPENE-1-CARBOXAMIDO)ETHYL]-2H-1-NAPHTHO[2,1-b]PYRAN

EXAMPLE 67
3,4-DIHYDRO-5-(2-PROPIONAMIDOETHYL)-2H-1-NAPHTHO[2,1-b]-PYRAN

EXAMPLE 68
3,4-DIHYDRO-5-(2-BUTYRAMIDOETHYL)-2H-1-NAPHTHO[2,1-b]PYRAN

EXAMPLE 69
3,4-DIHYDRO-5-(2-ISOBUTYRAMIDOETHYL)-2H-1-NAPHTHO[2,-b]-PYRAN

EXAMPLE 70
3,4-DIHYDRO-5-(2-TRIFLUOROACETAMIDOETHYL)-2H-1-NAPHTHO-[2,1-b]-PYRAN

EXAMPLE 71
3,4-DIHYDRO-5-(2-FORMAMIDOETHYL)-2H-1-NAPHTHO[2,1-b]PYRAN

EXAMPLE 72
3,4-DIHYDRO-5-(2-PENTANAMIDOETHYL)-2H-1-NAPHTHO[2,1-b]-PYRAN

EXAMPLE 73
3,4-DIHYDRO-5-[2-(IODOACETAMIDO)ETHYL]-2H-1-NAPHTHO[2,1-b]-PYRAN

EXAMPLE 74
3,4-DIHYDRO-5-[2-(CYCLOPROPANECARBOXAMIDO)ETHYL]-2H-1-NAPHTHO[2,1-b]PYRAN

EXAMPLE 75
3,4-DIHYDRO-5-[2-(CYCLOBUTANECARBOXAMIDO)ETHYL]-2H-1-NAPHTHO[2,1-b]PYRAN

EXAMPLE 76
3,4-DIHYDRO-5-[2-(CYCLOPENTANECARBOXAMIDO)ETHYL]-2H-1-NAPHTHO[2,1-b]PYRAN

EXAMPLE 77
3,4-DIHYDRO-5-[2-(CYCLOHEXANECARBOXAMIDO)ETHYL]-2H-1-NAPHTHO[2,1-b]PYRAN

EXAMPLE 78
3,4-DIHYDRO-5-[2-(PROPENE-1-CARBOXAMIDO)ETHYL]-2H-1-NAPHTHO[2,1-b]PYRAN

EXAMPLE 79
N-[2-(2,3-DIHYDRO-3-OXO-1-NAPHTHO[2,1-b]FURAN-4YL)ETHYL]-N'-METHYLUREA

EXAMPLE 80
N-[2-(2,3-DIHYDRO-3-OXO-1-NAPHTHO[2, 1-b]FURAN-4-YL)ETHYL]-N'-ETHYLUREA

EXAMPLE 81
N-[2-(2,3-DIHYDRO-3-OXO-1-NAPHTHO[2,1-b]FURAN-4YL)ETHYL]-N'-n-PROPYLUREA

EXAMPLE 82
N-[2-(2,3-DIHYDRO-3-OXO-1-NAPHTHO[2,1-b]FURAN-4-YL)ETHYL]-N'-CYCLOPROPYLUREA

EXAMPLE 83
N-[2-(2,3-DIHYDRO-3-OXO-1-NAPHTHO[2,1-b]FURAN-4-YL)ETHYL]-N'-n-PROPYLTHIOUREA

EXAMPLE 84
N-[2-(2,3-DIHYDRO-3-OXO-1-NAPHTHO[2,1-b]FURAN-4-YL)ETHYL]-N'-CYCLOPROPYLTHIOUREA

EXAMPLE 85
N-[2-(2,3-DIHYDRO-3-HYDROXY-1-NAPHTHO[2,1-b]FURAN-4-YLETHYL]-N'-METHYLUREA

EXAMPLE 86
N-[2-(2,3-DIHYDRO-3-HYDROXY-1-NAPHTHO[2,1-b]FURAN-4-YL)ETHYL]-N'-ETHYLUREA

EXAMPLE 87
N-[2-(2,3-DIHYDRO-3-HYDROXY-1-NAPHTHO[2,1-b]FURAN YL)ETHYL]-N'-PROPYLUREA

EXAMPLE 88
N-[2-(2,3-DIHYDRO-3-HYDROXY-1-NAPHTHO[2,1-b]FURAN-4YL)ETHYL]-N'-CYCLOPROPYLUREA

EXAMPLE 89
N-[2-(2,3-DIHYDRO-3-HYDROXY-1-NAPHTHO[2,1-b]FURAN-4-YL)ETHYL]-N'-PROPYLTHIOUREA

EXAMPLE 90
N-[2-(2,3-DIHYDRO-3-HYDROXY-1-NAPHTHO[2,1-b]FURAN-4-YL)ETHYL]-N'-CYCLOPROPYLTHIOUREA

EXAMPLE 91
N-[2-(1-NAPHTHO[2,1-b]FURAN-4-YL)ETHYL]-N'-METHYLUREA

EXAMPLE 92
N-[2-(1-NAPHTHO[2,1-b]FURAN-4-YL)ETHYL]-N'-ETHYLUREA

EXAMPLE 93
N-[2-(1-NAPHTHO[2,1-b]FURAN-4-YL)ETHYL]-N'-PROPYLUREA

EXAMPLE 94
N-[2-(1-NAPHTHO[2,1-b]FURAN-4-YL)ETHYL]-N'-CYCLOPROPYLUREA

EXAMPLE 95
N-[2-(1-NAPHTHO[2,1-b]FURAN-4-YL)ETHYL]-N'-PROPYLTHIOUREA

EXAMPLE 96
N-[2-(1-NAPHTHO[2,1-b]FURAN-4-YL)ETHYL]-N'-CYCLOPROPYLTHIOUREA

EXAMPLE 97
N-[2-(2H-1-NAPHTHO[2,1-b]PYRAN-5-YL)ETHYL]-N'-METHYLUREA

EXAMPLE 98
N-[2-(2H-1-NAPHTHO[2,1-b]PYRAN-5-YL)ETHYL]-N'-ETHYLUREA

EXAMPLE 99
N-[2-(2H-1-NAPHTHO[2,1-b]PYRAN-5-YL)ETHYL]-N'-n-PROPYLUREA

EXAMPLE 100
N-[2-(2H-1-NAPHTHO[2,1-b]PYRAN-5-YL)ETHYL]-N'-CYCLOPROPYLUREA

EXAMPLE 101
N-[2-(2H-1-NAPHTHO[2,1-b]PYRAN-5-YL)ETHYL]-N'-PROPYLTHIOUREA

EXAMPLE 102
N-[2-(2H-1-NAPHTHO[2,1-b]PYRAN-5-YL)ETHYL]-N'-CYCLOPROPYLTHIOUREA

EXAMPLE 103
N-[2-(3,4,5,6,7,8-HEXAHYDRO-2H-1-NAPHTHO[2,1-b]PYRAN-5-YL)ETHYL]-N'-METHYLUREA

EXAMPLE 104
N-[2-(3,4,5,6,7,8-HEXAHYDRO-2H-1-NAPHTHO[2,1-b]PYRAN-5-YL)ETHYL]-N'-ETHYLUREA

EXAMPLE 105
N-[2-(3,4,5,6,7,8-HEXAHYDRO-2H-1-NAPHTHO[2,1-b]PYRAN-5-YL)ETHYL]-N'-PROPYLUREA

EXAMPLE 106
N-[2-(3,4,5,6,7,8-HEXAHYDRO-2H-1-NAPHTHO[2,1-b]PYRAN-5-YL)ETHYL]-N'-CYCLOPROPYLUREA

EXAMPLE 107
N-[2-(3,4,5,6,7,8-HEXAHYDRO-2H-1-NAPHTHO[2,1-b]PYRAN-5-YL)ETHYL]-N'-PROPYLTHIOUREA

EXAMPLE 108
N-[2-(3,4,5,6,7,8-HEXAHYDRO-2H-1-NAPHTHO[2,1-b]PYRAN-5-YL)ETHYL]-N'-CYCLOPROPYLTHIOUREA

EXAMPLE 109
N-[2-(3,4-DIHYDRO-2H-1-NAPHTHO[2,1-b]PYRAN-5-YL)ETHYL]-N'-METHYLUREA

EXAMPLE 110
N-[2-(3,4-DIHYDRO-2H-1-NAPHTHO[2,1-b]PYRAN-5-YL)ETHYL]-N'-ETHYLUREA

EXAMPLE 111
N-[2-(3,4-DIHYDRO-2H-1-NAPHTHO[2,1-b]PYRAN-5-YL)ETHYL]-N'-PROPYLUREA

EXAMPLE 112
N-[2-(3,4-DIHYDRO-2H-1-NAPHTHO[2,1-b]PYRAN-5-YL)ETHYL]-N'-CYCLOPROPYLUREA

EXAMPLE 113
N-[2-(3,4-DIHYDRO-2H-1-NAPHTHO[2,1-b]PYRAN-5-YL)ETHYL]-N'-PROPYLTHIOUREA

EXAMPLE 114
N-[2-(3,4-DIHYDRO-2H-1-NAPHTHO[2,1-b]PYRAN-5-YL)ETHYL]-N'-CYCLOPROPYLTHIOUREA

EXAMPLE 115
N-[2-(7H-8,9-DIHYDROPYRANO[3,2-e]INDOLYL)ETHYL]ACETAMIDE

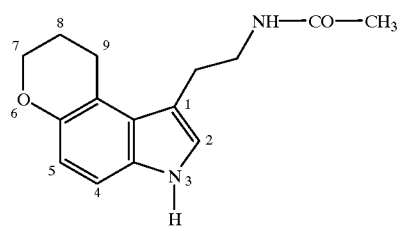

Example 115

By proceeding on the compound of Preparation 39 with acetyl chloride, the title compound is obtained.

EXAMPLES 116 TO 118

By proceeding as in Example 115, but using the appropriate acyl chloride, the compounds of the following examples are obtained:

EXAMPLE 116

N-[2-(7H-8,9-DIHYDROPYRANO[3,2-e]INDOLYL)ETHYL]-PROPIONAMIDE

EXAMPLE 117

N-[2-(7H-8,9-DIHYDROPYRANO[3,2-e]INDOLYL)ETHYL]CYCLOPROPANECARBOXAMIDE

EXAMPLE 118

N-[2-(7H-8,9-DIHYDROPYRANO[3,2-e]INDOLYL)ETHYL]CYCLOBUTANECARBOXAMIDE

EXAMPLE 119

2,3-DIHYDRO-2-METHYL-4-(2-ACETAMIDOETHYL)1-NAPHTHO[2,1-b]-FURAN

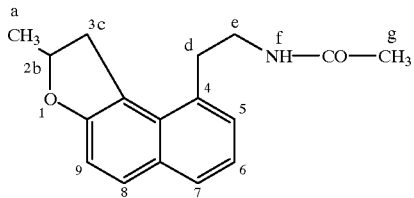

Reactants:
N-[2-(8-Allyl-7-hydroxynaphth-1-yl)ethyl]acetamide (Preparation 40): 3.7 mmol (1 g)
Trifluoroacetic acid (99%, d=1.48): 32 mmol (2.33 cm$^3$)
Procedure:

The compound from Preparation 40 is dissolved in the trifluoroacetic acid in a 50 cm$^3$ flask and the mixture is brought to reflux for 8 h. It is left to cool. The medium is evaporated to dryness and the residue is taken up in water and extracted with ethyl acetate (3×10 cm$^3$). The organic phase is washed with 2×2 cm$^3$ of a 10% aqueous sodium hydroxide solution and then with water. The organic phase is dried over MgSO$_4$ and brought to dryness. The product is purified on a silica column using acetone/toluene/cyclohexane as eluent.
Characteristics:
Molecular mass: 269.34 g for $C_{17}H_{19}NO_2$
Appearance: whitish solid
Melting point: 136° C.
R$_f$: 0.32 eluent: acetone/toluene/cyclohexane (4/4/2)
Yield: 73%
Recrystallization solvent: toluene/cyclohexane (1/3)

Infrared:

| 3240 and 3050 | cm$^{-1}$ | ν NH amide |
| 2960–2840 | cm$^{-1}$ | ν CH alkyls |
| 1630 | cm$^{-1}$ | ν CO amide |
| 1000-1580 | cm$^{-1}$ | ν C=C aromatics |

NMR (CDCl$_3$, δ) 300 MHz:

| 1.54 | ppm doublet | 3H H$_a$, | J$_{a-b}$ = 6.30 Hz |
| 1.96 | ppm singlet | 3H H$_g$ | |
| 3.29 | ppm multiplet | 2H H$_d$ | |
| 3.40 | ppm double doublet | 1H H$_c$"cis" | J = 7.6 Hz; J$_{c'-b}$ = 7,7 Hz; J$_{c'-c}$ = 15,2 Hz |
| 3.56 | ppm multiplet | 2H H$_e$ | |
| 3.94 | ppm double doublet | 1H H$_c$"trans" | J = 9.2 Hz; J$_{c'-c}$ = 15,2 Hz |
| 5.05–5.07 | ppm unresolved peak | 1H H$_b$ | |
| 5.53 | ppm signal | 1H H$_f$ | |
| 7.08–7.23 | ppm unresolved peak | 3H, aromatic protons, H$_5$, H$_6$, H$_9$ | |
| 7.67–7.70 | ppm unresolved peak | 2H, aromatic protons, H$_8$, H$_7$ | |

EXAMPLE 120

N-[2-(2,3-DIHYDRO-2-METHYL-1-NAPHTHO[2,1-b]FURAN-4-YL)ETHYL]-N'-METHYLUREA

By proceeding as in Example 119, but using the compound from Preparation 41 at the start, the title product is obtained.
Melting point: 165–169° C.

EXAMPLES 121 TO 130

EXAMPLE 121

N-[2-(7H-8,9-DIHYDROTHIENO[3,2-f]BENZOTHIOPYRAN-1-YL)ETHYL]-ACETAMIDE

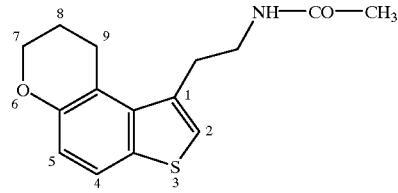

EXAMPLE 122

N-[2-(7H-8,9-DIHYDRO-THIENO[3,2-f]BENZOPYRAN-1-YL)ETHYL]-PROPIONAMIDE

EXAMPLE 123

N-[2-(7H-8,9-DIHYDRO-THIENO[3,2-f]BENZOPYRAN-1-YL)ETHYL]-CYCLOPROPANECARBOXAMIDE

EXAMPLE 124

N-[2-(7H-8,9-DIHYDRO-THIENO[3,2-f]BENZOPYRAN-1-YL)ETHYL]-CYCLOBUTANECARBOXAMIDE

EXAMPLE 125

N-[2-(7H-8,9-DIHYDRO-THIENO[3,2-f]BENZOPYRAN-1-YL)ETHYL]-TRIFLUOROACETAMIDE

EXAMPLE 126

N-[2-(7H-8,9-DIHYDRO-FURO[3,2-f]BENZOPYRAN-1-YL)ETHYL]-ACETAMIDE

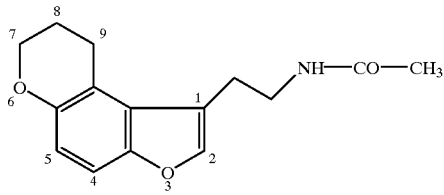

EXAMPLE 127

N-[2-(7H-8,9-DIHYDROFURO[3,2-f]BENZOPYRAN-1-YL)ETHYL]-PROPIONAMIDE

EXAMPLE 128

N-[2-(7H-8,9-DIHYDROFURO[3,2-f]BENZOPYRAN-1-YL)ETHYL]-CYCLOPROPANECARBOXAMIDE

EXAMPLE 129

N-[2-(7H-8,9-DIHYDROFURO[3,2-f]BENZOPYRAN-1-YL)ETHYL]-CYCLOBUTANECARBOXAMIDE

EXAMPLE 130

N-[2-(7H-8,9-DIHYDROFURO[3,2-f]BENZOPYRAN-1-YL)ETHYL]-TRIFLUOROACETAMIDE

PREPARATION 42

2-(8,9-Dihydro-7H-furo[3,2-f]chromen-1-yl)ethylamine

Stage A: 5-Methoxy-2,3-dihydrobenzo[b]furan-3-one

Under inert atmosphere, 0.08 mol (1.85 g) of metallic sodium are dissolved in 80 ml of anhydrous methanol. When all sodium is dissolved, the methanol is evaporated and the sodium methanolate thus obtained is dissolved in 300 ml of anhydrous toluene, then 80 mmol (20 g) of methyl 5-methoxy-2-(2-methoxy-2-oxoetoxy) benzoate are added. The reaction mixture is refluxed 35 minutes. The toluene is evaporated and the residue is dissolved in water. The solution is acidified with concentrated chlorhydric acid until pH=1, and the precipitate is filtered. The solid thus obtained is dissolved in 300 ml of methanol and 200 ml of NaOH 30% are added, and the mixture is refluxed 5 hours. After cooling, the methanol is evaporated and the mixture diluted with water and acidified with concentrated chlorhydric acid until pH=1. The red precipitate thus obtained is filtered, washed with water and recrystallized in water/ethanol.

MP=92° C.

Stage B: 2-(5-Methoxybenzo[b]furan-3-yl)acetonitrile

Under inert atmosphere, 83 mmol of sodium hydride are suspended in 100 ml of anhydrous THF. The temperature is cooled at −15° C. and 83 mmol (14.7 g) of (EtO)$_2$POCH$_2$CN in 50 ml of 1BF are droply added. Then 55 mmol (9 g) of compound obtained in stage A in 100 ml of THF are dropwised at −15° C. The solution is stirred during 2 hours at that temperature before being hydrolysed. The mixture is extracted with ethyl acetate and the organic layers are washed with brine, dried over magnesium sulfate and concentrated. The title product is obtained after purification by chromatography on silica gel.

Stage C: 2-[5-(Hydroxybenzo[b]furan-3-yl)acetonitrile

Under inert atmosphere, 38 mmol (7.1 g) of compound obtained in stage B are dissolved in 140 ml of CH$_2$Cl$_2$. The mixture is cooled with an ice bath and 76 mmol (7.3 ml) of BBr$_3$ are added. The reaction mixture is stirred at room temperature 5 hours, then hydrolysed with ice/water and extrated with CH$_2$Cl$_2$. The organic layer is washed with water, dried on magnesium sulfate and concentrated to yield the title product.

MP=110° C.

Stage D: 2-[5-(Cyanomethoxy)benzo[b]furan-3-yl]acetonitrile

To a solution of 33 mmol of phenol obtained in stage C in 150 ml of acetone are added 100 mmol (13.8 g) of potassium carbonate. The mixture is refluxed 15 minutes and 100 mmol (8.9 ml) of propargyl bromide are added. The reaction is refluxed overnight. After cooling, the reaction mixture is filtered and the filtrate is concentrated. The residue is dissolved in a mixture of water/ethylacetate and after extraction, the organic layers are washed successively by NaOH 10% and brine, dried over magnesium sulfate and concentrated. The title product is obtained by chromatography on silica gel.

MP=86–87° C.

Stage E: 2-(7H-Furo[3,2-f]chromen-1-yl]acetonitrile

A mixture of 0.03 mol (6 g) of compound obtained in stage D in 170 ml of triethyleneglycol is refluxed 5 minutes. The reaction is then cooled at room temperature and hydrolysed by a mixture water/ice. The precipitate thus formed is filtrated and recrystallized in isopropanol to yield the title product.

MP=99–101° C.

Stage F: 2-(8,9-Dihydro-7H-furo[3,2-f]chromen-1-yl)ethylamine 1.4 mmol of compound obtained in stage E are dissolved in 30 ml of ethanol saturated with ammonia, in the presence of 400 mg of Nickel (Raney). The reaction mixture is stirred at 50° C. under 50 atm of hydrogen during 5 hours. After cooling and filtration of the catalyst, the filtrate is concentrated, dissolved in a mixture of ether/water and extracted. The organic layer is dried over magnesium sulfate and concentrated to yield the title product.

MP (HCl)=160° C.

PREPARATION 43

2-(8,9-Dihydro-7H-thieno[3,2-f]chromen-1-yl)ethylamine

The procedure is the same as that of Preparation 42 using as starting material methyl 5-methoxy-2-[(2-methoxy-2-oxoethyl)thio]benzoate.

PREPARATION 44

2-(3,7,8,9-Tetrahydropyrano[3,2-e]indol-1-yl)ethylamine

The procedure is the same as that of Preparation 42 using as starting material methyl 5-methoxy-2-[(2-methoxy-2-oxoethyl)amino]benzoate.

PREPARATION 45

N-{2-[5-(Cyanomethoxy)benzo[b]furan-3-yl]
ethyl}acetamide

Stage A: N-[2-(5-Methoxybenzo[b]furan-3-yl)ethyl]
acetamide

A solution of 18.7 mmol (3.5 g) of compound obtained in stage B of Preparation 42 in 80 ml of acetic anhydride is stirred under 60 atm of hydrogen at 60° C., with 0.4 g of Nickel (Raney) during 6 hours. After cooling, the catalyst is filtered and rinsed with ethanol. The filtrate is concentrated and dissolved in ethyl acetate and stirred into NaOH 30% during 30 minutes. After extraction, the organic layer is washed with brine, dried over magnesium sulfate and concentrated. The title product is recrystallized in toluene.

MP=113° C.

Stage B: N-[2-(5-Hydroxybenzo[b]furan-3-yl)ethyl]
acetamide

The procedure is the same as that used in stage C of Preparation 42.

MP=115° C.

Stage C: N-{2-[5-(Cyanomethoxy)benzo[b]furan-3-yl]
ethyl}acetamide

To a solution of 4.1 mmol of compound obtained in stage B in 30 ml of acetone are added 12.3 mmol (1.7 g) of potassium carbonate, and the mixture is warmed to reflux during 15 minutes. Propargyl bromide (12.5 mmol, 1.35 ml) is added and the reaction is refluxed during 6 hours. After cooling, the mixture is filtered and the filtrate concentrated. The residue thus obtained is dissolved in ethyl acetate, washed with water, then with NaOHIM, and with brine. The organic layer is dried over magnesium sulfate, concentrated and the solid obtained recrystallized in toluene/cyclohexane to yield the title product.

MP=72–73° C.

PREPARATION 46

N-[2-(4-Allyl-5-hydroxybenzo[b]furan-3-yl)ethyl]
acetamide

The procedure is the same as that used in stages C and D of Preparation 40 from the compound obtained in stage B of Preparation 45.

PREPARATION 47

N-[2-(5-Carboxymethyloxybenzo[b]furan-3-yl)
ethyl]acetamide

The procedure is the same as that used in Preparation 1 from the compound obtained in stage B of Preparation 45.

EXAMPLE 131

N-[2-(8,9-Dihydro-7H-furo[3,2-f]chromen-1-yl)
ethyl]acetamide

To a solution of 0.67 mmol of the hydrochloride of the amine obtained in Preparation 42 in 18 ml of chloroform and 6 ml of water are added 1.5 mmol of potassium carbonate and 0.84 mmol of acetylchloride. The mixture is stirred vigorously for 30 minutes, then extracted. The organic layer is dried over magnesium sulfate and concentrated to yield the title product.

MP=162° C.

| | Microanalysis: | | |
|---|---|---|---|
| | C | H | N |
| % Calculated | 69.48 | 6.61 | 5.40 |
| % Found | 69.62 | 6.30 | 5.24 |

The compounds of Examples 132 to 139 are obtained using the same procedure as in Example 131 and the appropriate acid chloride.

EXAMPLE 132

N-[2-(8,9-Dihydro-7H-furo[3,2-f]chromen-1-yl)
ethyl]propanamide

EXAMPLE 133

N-[2-(8,9-Dihydro-7H-furo[3,2-f]chromen-1-yl)
ethyl]-1-cyclopropane carboxamide

EXAMPLE 134

N-[2-(8,9-Dihydro-7H-furo[3,2-f]chromen-1-yl)
ethyl]-1-cyclobutane carboxamide

EXAMPLE 135

N-[2-(8,9-Dihydro-7H-furo[3,2-f]chromen-1-yl)
ethyl]-2,2,2-trifluoroacetamide

EXAMPLE 136

N-[2-(8,9-Dihydro-7H-furo[3,2-f]chromen-1-yl)
ethyl]acrylamide

MP=104–106° C.

EXAMPLE 137

N-[2-(8,9-Dihydro-7H-furo[3,2-f]chromen-1-yl)
ethyl]-2-iodoacetamide

MP=131° C.

EXAMPLE 138

N-[2-(8,9-Dihydro 7H-furo[3,2-f]chromen-1-yl)
ethyl]-2-butenamide

MP=137° C.

EXAMPLE 139

N-[2-(8,9-Dihydro-7H-furo[3,2-f]chromen-1-yl)
ethyl]-3-butenamide

MP=104° C.

Examples 140 to 144 are prepared using the same procedure as in Example 131, from the compound obtained in Preparation 43 and the appropriate acid chloride.

EXAMPLE 140

N-[2-(8,9-Dihydro-7H-thieno[3,2-f]chromen-1-yl)
ethyl]acetamide

EXAMPLE 141

N-[2-(8,9-Dihydro-7H-thieno[3,2-f]chromen-1-yl)
ethyl]propanamide

EXAMPLE 142

N-[2-(8,9-Dihydro-7H-thieno[3,2-f]chromen-1-yl)
ethyl]-1-cyclopropane carboxamide

EXAMPLE 143

N-[2-(8,9-Dihydro-7H-thieno[3,2-f]chromen-1-yl)
ethyl]-1-cyclobutane carboxamide

EXAMPLE 144

N-[2-(8,9-Dihydro-7H-thieno[3,2-f]chromen-1-yl)
ethyl]-2,2,2-trifluoroacetamide

Examples 145 to 148 are prepared using the same procedure as in Example 131, from the compound obtained in Preparation 44 and the appropriate acid chloride.

EXAMPLE 145

N-[2-(3,7,8,9-Tetrahydropyrano[3,2-e]indol-1-yl)
ethyl]acetamide

EXAMPLE 146

N-[2-(3,7,8,9-Tetrahydropyrano[3,2-e]indol-1-yl)
ethyl]propanamide

EXAMPLE 147

N-[2-(3,7,8,9-Tetrahydropyrano[3,2-e]indol-1-yl)
ethyl]-1-cyclopropane carboxamide

EXAMPLE 148

N-[2-(3,7,8,9-Tetrahydropyrano[3,2-e]indol-1-yl)
ethyl]-1-cyclobutane carboxamide

EXAMPLE 149

N-[12-(8,9-Dihydro-7H-furo[3,2-f]chromen-1-yl)
ethyl]N-methylacetamide

The compound obtained in Example 131 is treated with sodium hydride and methyl iodide to yield the title product.
MP=82° C.

EXAMPLE 150

N-[2-(7H-Furo[3,2-f]chromen-1-yl)ethyl]acetamide

A solution of 1.95 mmol of the compound obtained in Preparation 45 in 20 ml of triethylene glycol is warmed to 280° C. during 16 minutes. After cooling, the mixture is dissolved in water and ethylacetate and extracted with ethylacetate. The organic layer is washed with brine, dried over magnesium sulfate, concentrated and purified by chromatography on silica gel.
MP=129° C.

|  | Microanalysis | | |
| --- | --- | --- | --- |
|  | C | H | N |
| % Calculated | 70.02 | 5.87 | 5.44 |
| % Found | 69.82 | 6.10 | 5.54 |

EXAMPLE 151

N-[2-(7-Oxo-7,8-dihydrofuro[3',2':3,4]benzo[b]
furan-1-yl)ethyl]acetamide

The procedure is the same as that used in Example 1 from the compound obtained in Preparation 47.

EXAMPLE 152

N-[2-(7-Hydroxy-7,8-dihydrofuro[3',2':3,4]benzo[b]
furan-1-yl)ethyl]acetamide

The procedure is the same as that used in Example 2 from the compound obtained in Example 151.

EXAMPLE 153

N-[2-(7-Methyl-7,8-dihydrofuro[3',2':3,4]benzo[b]
furan-1-yl)ethyl]acetamide

The procedure is the same as that used in Example 119 from the compound obtained in Preparation 46.

EXAMPLE 154

N-[2-(8,9-Dihydro-7H-furo[3,2-chromen-1-yl)
ethyl]-N'-methylurea

To a suspension of 0.01 mole of 2-(8,9-dihydro-7H-furo[3,2-f]chromen-1-yl)ethylamine hydrochloride in five (5) ml of pyridine, 0.011 mole of methylisocyanate is added dropwise with stirring. The reaction mixture is stirred for one (1) hour at 80° C., then poured on ice/water. After classical work up and purification, the title compound is obtained.

Examples 155 to 158 are obtained using the same procedure as in Example 154.

EXAMPLE 155

N-[2-(8,9-Dihydro-7H-furo[3,2-f]chromen-1-yl)
ethyl]-N'-isopropylurea

This compound is prepared by reacting the compound of Preparation 42 (hydrochloride) and isopropyl isocyanate.

EXAMPLE 156

N-Cyclobutyl-N'-[2-(8,9-dihydro-7H-furo[3,2-f]
chromen-1-yl)ethyl]urea

This compound is prepared by reacting the compound of Preparation 42 (hydrochloride) and cyclobutyl isocyanate.

EXAMPLE 157

N-[2-(8,9-Dihydro-7H-thieno(3,2-f]chromen-1-yl)
ethyl]-N'-methylurea

This compound is prepared by reacting the compound of Preparation 43 (hydrochloride) and methyl isocyanate.

EXAMPLE 158

N-Methyl-N'-[2-(3,7,8,9-tetrahydropyrano[3,2-f]
indol-1-yl)ethyl]urea

This compound is prepared by reacting the compound of Preparation 44 (hydrochloride) and methyl isocyanate.

It is to be noted that Examples 131, 132, 133, 134, and 135 yield the identical products as Examples 126, 127, 128, 129, and 130, and that Examples 140, 141, 142, 143, 144, 145, 146, 147, and 148 yield the identical products as Examples 121, 122, 123, 124, 125, 115, 116, 117, and 118, although the nomenclature employed for naming of the said products is different.

EXAMPLE 159

N-[2-(8,9-Dihydro-7H-furo[3,2-f]chromen-1-yl)
ethyl]-N'-propylurea: MP=165° C.

This compound is prepared according to the procedure of Example 154 by reacting the compound of Preparation 42 as its hydrochloride with propylisocyanate.

EXAMPLE 160

N-Butyl-N'-[2-(8,9-dihydro-7H-furo[3,2-f]chromen-1-yl)ethyl)urea: MP=132–133° C.

This compound is prepared according to the procedure of Example 154 by reacting the compound of Preparation 42 as its hydrochloride with butylisocyanate.

EXAMPLE 161

N-Cyclopropyl-N'-[2-(8,9-dihydro-7H-furo[3,2-f]chromen-1-yl)ethyl]thiourea: MP=160–161° C.

This compound is prepared according to the procedure of Example 154 by reacting the compound of Preparation 42 as its hydrochloride with cyclopropylisocyanate.

EXAMPLE 162

N-[2-(8,9-Dihydro-7H-furo[3,2-f]chromen-1-yl)ethyl]-N'-propylthiourea: MP=100° C.

This compound is prepared according to the procedure of Example 154 by reacting the compound of Preparation 42 as its hydrochloride with propylisothiocyanate.

EXAMPLE 163

N-Butyl-N'-[2-(8,9-dihydro-7H-furo[3,2-f]chromen-1-yl)ethyl]thiourea: MP=121–122° C.

This compound is prepared according to the procedure of Example 154 by reacting the compound of Preparation 42 as its hydrochloride with butylisothiocyanate.

PHARMACOLOGICAL STUDY

EXAMPLE A

Study of the Acute Toxicity

The acute toxicity was assessed after oral administration to batches of 8 mice (26±2 grams). The animals were observed at regular intervals during the first day and daily during the two weeks following the treatment. The $LD_{50}$, resulting in the death of 50% of the animals, was evaluated.

The $LD_{50}$ of the products tested is greater than 1000 mg.kg$^{-1}$ for the compounds studied, which indicates the low toxicity of the compounds of the invention.

EXAMPLE B

Study of the Binding to Melatonin Receptors

B1) Study on Sheep Pars Tuberalis Cells

Studies of the binding of the compounds of the invention to melatonin receptors were carried out according to conventional techniques on sheep pars tuberalis cells. The pars tuberalis of the adenohypophysis is in fact characterized, in mammals, by a high density of melatonin receptors (Journal of Neuroendocrinology, 1, pp 1–4, 1989).

Protocol

1) Sheep pars tuberalis membranes are prepared and used as target tissue in saturation experiments in order to determine the binding capacities and affinities for 2-($^{125}$I) iodomelatonin.

2) Sheep pars tuberalis membranes are used as target tissue, with the various compounds to be tested, in competitive binding experiments with respect to 2-iodo-melatonin.

Each experiment is carried out in triplicate and a range of different concentrations is tested for each compound.

The results make it possible to determine, after statistical treatment, the binding affinities of the compound tested.

Results

It appears that the compounds of the invention have a very high affinity for melatonin receptors. In particular, the compound of Example 119 has an extremely powerful affinity for melatonin receptors, with an $IC_{50}$ of $6.9 \times 10^{-15}$ M.

B2) Study on Chicken Brain Cell Membranes (*Gallus domesticus*)

The animals used are 12-day old chickens (*Gallus domesticus*). They are sacrificed between 1300 and 1700 hours on the day of their arrival. The brains are quickly removed and frozen at –200° C. and then stored at –80° C. The membranes are prepared according to the method described by Yuan and Pang (Journal of Endocrinology, 128. pages 475–482, 1991). 2-($^{125}$I)Iodomelatonin is incubated in the presence of the membranes in a buffered solution at pH 7.4 for 60 min at 25° C. At the end of this period, the membrane suspension is filtered (Whatman GF/C). The radioactivity retained on the filter is determined using a Beckman® LS 6000 liquid scintillation counter.

The products used are:

2-($^{125}$I)iodomelatonin melatonin compounds of the invention

In primary screening, the molecules are tested at 2 concentrations ($10^{-7}$ and $10^{-5}$ M). Each result is the mean of 3 independent measurements. The active molecules retained after the results of the primary screening were made the subject of a quantitative determination of their efficiency ($IC_{50}$). They are used at 10 different concentrations.

Thus, the $IC_{50}$ values found for the preferred compounds of the invention, which correspond to the values of the affinity, show that the binding of the compounds tested is very powerful.

EXAMPLE C

Four Plates Test

The products of the invention are administered via the esophagus to batches of ten mice. One batch receives acacia syrup. 30 minutes after administration of the test products, the animals are placed in compartments, the floor of which comprises four metal plates. Every time the animal passes from one plate to another, it receives a mild electric shock (0.35 mA). The number of transfers from one plate to another is recorded during one minute. After administration, the compounds of the invention significantly increase the number of transfers from one plate to another, demonstrating the anxiolytic activity of the compounds of the invention.

EXAMPLE D

Compounds of the Invention on the Circadian Rhythms of Rat Locomotory Activity The involvement of melatonin in controlling, by day/night alternation, the majority of the physiological, biochemical and behavioral circadian rhythms has made it possible to establish a pharmacological model for researching melatoninergic ligands.

The effects of the molecules are tested on many parameters and in particular on the circadian rhythms of locomotory activity which represent a reliable marker for the activity of the endogenous circadian clock.

In this study, the effects of these molecules on a specific experimental model, namely the rat placed in temporal isolation (permanent darkness), were evaluated.

Protocol

Male Long Evans rats, aged one month, are subjected, from their arrival in the laboratory, to a light cycle of 12 h of light per 24 h (LD 12:12).

After adapting for 2 to 3 weeks, they are placed in cages equipped with a wheel connected to a recording system in order to detect the phases of locomotory activity and thus to monitor the nyctohemeral (LD) or circadian (DD) rhythms.

As soon as the rhythms recorded testify to stable control by the light cycle LD 12:12, the rats are placed in permanent darkness (DD).

Two to three weeks later, when the free mode (rhythm reflecting that of the endogenous clock) is clearly established, the rats receive a daily administration of the test molecule.

The observations are carried out by making visible the rhythms of activity:
control of the rhythms of activity by the light rhythm,
disappearance of rhythm control in permanent darkness,
control by the daily administration of the molecule; transitory or lasting effect.

A computer program makes it possible:
to measure the duration and the intensity of the activity, and the period of the rhythm in animals in free mode and during the treatment,
optionally to demonstrate, by spectral analysis, the existence of circadian and noncircadian (ultradien, for example) components.

Results

It clearly appears that the compounds of the invention make it possible to have a powerful effect on the circadian rhythm via the melatoninergic system.

EXAMPLE E

Antiarrhythmic Activity

Protocol
(Ref: Lawson J. W. et al., J. Pharmacol. Expert. Therap., 160, 22–31, 1968)

The substance tested is administered intraperitoneally to a group of 3 mice 30 min before exposure to anesthesia by chloroform. The animals are then observed for 15 min. The absence of any recording of arrhythmias and of heart rates above 200 beats/min (control: 400–480 beats/min) in two animals at least indicates significant protection.

EXAMPLE F

Platelet Aggregation-Inhibitory Activity Protocol
(Ref.: Bertele V. et al., Science, 220, 517–519, 1983
ibid, Eur. J. Pharmacol., 85, 331–333, 1982)

The compounds of the invention (100 μg/mi) are tested for their ability to inhibit the irreversible platelet aggregation induced by sodium arachidonate (50 μg(ml) in platelet-enriched rabbit plasma.

Inhibition of the maximum aggregation by more than 50% indicates significant activity for the compounds of the invention.

This in vitro test shows that the compounds of the invention are good candidates for the treatment of cardiovascular diseases, in particular thromboses.

EXAMPLE G

Extension of the Bleeding Time

Protocol
(Ref.: Djana E. et al., Thrombosis Research, 15, 191–197, 1979) Butler K. D. et al., Thromb. Haemostasis, 47, 4649, 1982)

The test compounds are administered orally (100 mg/kg) to a group of 5 mice 1 h before standardized sectioning of the end of each tail (0.5 mm).

The mice are immediately suspended vertically, their tails being immersed for a length of 2 cm in a test tube containing an isotonic saline solution at 37° C.

The time required for the bleeding to stop for a period of 15 seconds is then determined.

An extension in the bleeding time of more then 50% relative to a group of control animals is regarded as significant for the compounds of the invention.

This in viva test confirms the benefit of the compounds of the invention in the treatment of cardiovascular pathologies since the compounds of the invention extend the bleeding time.

EXAMPLE H

Hypobaric Hypoxia Test

Protocol
(Ref.: Gotti B. and Depoortere H., Circ. Cerebrale, Congres de Circulation Cerebrale (Cerebral Circulation Congress], Toulouse, 105–107, 1979)

The test compounds are administered intraperitoneally (100 mg/kg) to a group of 3 mice 30 minutes before being placed in a chamber at a hypobaric pressure of 20 cm Hg.

The extension in the survival time, with respect to a group of animals treated with the vehicle, of more than 100% and in the absence of a depressant effect on the central nervous system indicates a cerebral protective activity of the compounds of the invention.

EXAMPLE I

Effects in the free exploratory test in C3H/He mice

Apparatus and procedure:
Behavior was assessed in a box subdivided into six equal square exploratory units, which were interconnected by small doors. It could be divided in half lengthwise by closing partitions. Twenty-four hours before the test, each animal was randomly placed in one half of the apparatus, with the temporary partitions in place, in order to become familiarized with it.

On the day of the test, the temporary partitions were removed and the animals were observed for 10 minutes:
numbers of attempts towards the unfamiliar compartment
latency of the first entry into the unfamiliar compartment
time spent in the unfamiliar compartment
locomotion in the unfamiliar compartment
number of rears in the unfamiliar compartment
locomotion in the familiar compartment
number of rears in the familiar compartment Experimental conditions:
Compounds were orally administered at doses of 1.5, and 25 mg/kg (in 1% HEC), 40 minutes before the test.

The central group received the vehicle under the same conditions.

Results:
Compounds were found to have desinhibitory effects in C3H/He mice, since they dose-dependently reduced the neophobia induced by an unfamiliar environment.

For example, the compound of Example 131 dose-dependently reduced the attempts and the latency, and increased the locomotion in the unfamiliar compartment. The differences with the control group were statistically significant for the 3 tested doses.

At 5 and 25 mg/kg, the compound of Example 131 significantly increased the time spent in the unfamiliar compartment.

At the highest dose, i.e., 25 mg/kg, the compound of Example 131 significantly increased the number of rears in the unfamiliar compartment.

Example II: Carbamides or Ureas

Substitution of the compounds of Examples 120 or 159–163 in the foregoing pharmacological Examples, especially in place of the compounds of Examples 119 and 131, gives approximately equally statistically-significant results.

EXAMPLE J

Pharmaceutical Composition: Tablets 1000 tablets, containing a dose of 5 mg of 5-(2-acetamidoethyl)-2H-1-naphtho[2,1-b]pyran 5-(2-Acetamidoethyl)-2H-1-naphtho[2, 1-b]pyran . . . 5 g
Wheat starch . . . 20 g
Maize starch . . . 20 g
Lactose . . . 30 g
Magnesium stearate . . . 2 g
Silica . . . 1 g
Hydroxypropylcellulose . . . 2 g

EXAMPLE K

Pharmaceutical Composition: Tablets 1000 tablets, containing a dose of 5 mg of N-[2-(8,9-Dihydro-7H-furo[3,2-f]chromen-1-yl) ethyl]acetamide N-[2-(8,9-Dihydro-7H-furo[3,2-f]chromen-1-yl)ethyl] acetamide . . . 5
Wheat starch . . . 20 g
Maize starch . . . 20 g
Lactose . . . 30 g
Magnesium stearate . . . 2 g
Silica . . . 1 g
Hydroxypropylcellulose . . . 2 g

EXAMPLE KK

Carbamides or Ureas

Substitution of the compounds of Examples 120 or 159–163 as the active ingredient in the compositions of Example J and Example K, in the same amounts, provides equally satisfactory pharmaceutical compositions of these carbamide or urea compounds.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

We claim:

1. A compound selected from those of formula (I):

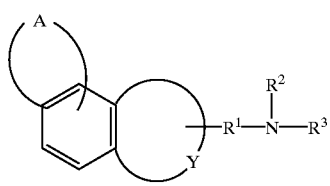

(I)

in which:

$R^1$ represents a (C$_1$–C$_4$) alkylene chain which is unsubstituted or substituted by a radical chosen from alkyl, hydroxyl, alkoxycarbonyl, and carboxyl;

$R^2$ represents hydrogen or alkyl;

$R^3$ represents a group of formula $R^{32}$:

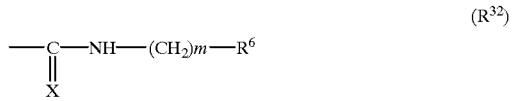

(R$^{32}$)

in which X represents oxygen or sulfur, m represents zero or 1 to 3, inclusive, and $R^6$ represents a radical chosen from hydrogen, unsubstituted or substituted alkyl, unsubstituted or substituted alkenyl, unsubstituted or substituted alkynyl, unsubstituted or substituted cycloalkyl, and unsubstituted or substituted dicycloalkylalkyl;

A represents a chain of formula —O—A$^1$ in which A$^1$ is a chain chosen from (C$_2$–C$_5$)alkylene, (C$_2$–C$_5$) alkenylene, and (C$_2$–C$_5$)alkynylene; A$^1$ being unsubstituted or substituted by one or a number of groups chosen from alkyl, alkoxy, hydroxyl, and oxo;

Y forming, with the benzene ring to which it is bonded, a Y$^1$ group selected from the group consisting of naphthalene, partially hydrogenated naphthalene, benzofuran, partially hydrogenated benzofuran, benzothiophene, partially hydrogenated benzothiophene, and indole;

it being understood that:

the expression "substituted" relating to the terms "alkyl", "alkenyl", and "alkynyl" means that these groups are substituted by one or a number of radicals chosen from halogen, alkyl, and alkoxy, the expression "substituted" relating to the term "cycloalkyl" or "dicycloalkylalkyl" means that these groups are substituted by one or a number of radicals chosen from: alkyl, alkoxy, hydroxyl, and the oxo group, the terms "alkyl" and "alkoxy" denote radicals containing 1 to 6 carbon atoms, inclusive, the terms "alkeniyl" and "alkynyl" denote unsaturated radicals having 2 to 6 carbon atoms, inclusive, the term "cycloalkyl" denotes a saturated or unsaturated cycloalkyl group having 3 to 8 carbon atoms, inclusive, its enantiomers and diastereoisomers, and an addition salt thereof with a pharmaceutically-acceptable base.

2. A compound of claim 1, which is N-[2-(2,3-dihydro-2-methyl-1-naphtho[2,1-b]furan-4-yl)ethyl]-N'-methylurea.

3. A compound of claim 1, which is N-[2-(8,9-Dihydro-7H-furo[3,2-f]chromen-1-yl)ethyl]-N'-propylurea.

4. A compound of claim 1, which is N-Butyl-N'-[2-(8,9-dihydro-7H-furo[3,2-f]chromen-1-yl)ethyl]urea.

5. A compound of claim 1, which is N-Cyclopropyl-N'-[2-(8,9-dihydro-7H-furo[3,2-f]chromen-1-yl)ethyl]thiourea.

6. A compound of claim 1, which is N-[2-(8,9-Dihydro-7H-furo[3,2-f]chromen-1-yl)ethyl]-N'-propylthiourea.

7. A compound of claim 1, which is N-Butyl-N'-[2-(8,9-dihydro-7H-furo[3,2-f]chromen-1-yl)ethyl]thiourea.

8. A compound of claim 1, which is N-[2-(8,9-Dihydro-7H-furo[3,2-f]chromen-1-yl)ethyl]-N'-methylurea.

9. A compound of claim 1, which is N-[2-(8,9-Dihydro-7H-furo[3,2-f]chromen-1-yl)ethyl]-N'-isopropylurea.

10. A compound of claim 1, which is N-Cyclobutyl-N'-[2-(8,9-dihydro-7H-furo[3,2-f]chromen-1-yl)ethyl]urea.

11. A compound as claimed in claim 1, wherein Y$^1$ is a benzofuran group.

12. A compound as claimed in claim 1, wherein Y$^1$ is a partially-hydrogenated benzofuran group.

13. A pharmaceutical composition containing a compound of claim 1 in combination with one or a number of pharmaceutically-acceptable excipients.

14. A method of treating a mammal afflicted with a disorder of the melatoninergic system comprising the step of administering to the said mammal an amount of a compound as claimed in claim 1 which is effective to alleviate the said disorder.

* * * * *

UNITED STATES PATENT AND TRADEMARK OFFICE
CERTIFICATE OF CORRECTION

PATENT NO. : 6,071,946
DATED : June 6, 2000
INVENTOR(S) : D. Lesieu, P. Depreux, V. Leclec, H.A. Mansour, P. Delagrange, P. Renard It is certified that error appears in the above-identified patent and that said Letters Patent is hereby corrected as shown below:

Column 1,
Line 25: "10" should be deleted.

Column 11,
Line 63: "$H_5$, $J_{-6}$= 9.00 Hz" should read: -- $H_5$, $J_{5-6}$= 9.00 Hz -- .

Column 15,
Line 33: At the beginning of the line, "9.5" should read: -- 9.8 --.

Column 18,
Line 29: In the Example title, at the end of the line, "-(2-" should read: -- -4-(2- --.

Column 23,
Line 57: At the end of the line, "-(2-" should read: -- -4-(2- --.
Line 65: At the end of the line, "4 (2-" should read -- -4-(2- --.

Column 24,
Line 2: At the end of the line, "4 (2-" should read: -- -4-(2- --.
Line 31: "-[2-" should read: -- -4-[2- --.

Column 26,
Line 34: " [2,b] -" should read -- [2,1-b] - --.

Column 27,
Line 30: "[2,1-b]FURAN YL)" should read: -- [2,1-b]FURAN-4-YL)- --.

Column 31,
Line 63: "IBF" should read -- THF --.

Column 35,
Line 35: At the beginning of the line, "N-[12-" should read -- N-[2- --.

Column 36,
Line 16(approx): "[3,2-" should read: -- [3,2-f] --.
Line 49: At the end of the line, "[3,2-f]" should read: -- [3,2-e] --.

UNITED STATES PATENT AND TRADEMARK OFFICE
CERTIFICATE OF CORRECTION

PATENT NO. : 6,071,946
DATED : June 6, 2000
INVENTOR(S) : D. Lesieu, P. Depreux, V. Leclec, H.A. Mansour, P. Delagrange, P. Renard It is certified that error appears in the above-identified patent and that said Letters Patent is hereby corrected as shown below:

Column 39,
Line 46: At the end of the line, "Protocol" should begin a new line.
Line 49: "(100 ug/mi)" should read: -- (100 ug/ml) --.
Line 51: "(50 ug(ml)" should read: -- (50 ug/ml) --.
Line 63: "4649," should read: -- 46-49,--.

Column 40,
Line 9: "in viva" should read: -- in vivo --.

Column 42,
Line 40: "alkeniyl" should read: -- "alkenyl" --.

Signed and Sealed this

Fourth Day of September, 2001

*Attest:*

NICHOLAS P. GODICI
*Attesting Officer*     *Acting Director of the United States Patent and Trademark Office*